(12) United States Patent
Vogt et al.

(10) Patent No.: US 10,765,463 B2
(45) Date of Patent: Sep. 8, 2020

(54) BONE CEMENT APPLICATOR WITH PIPE LINE ELEMENT AND CLOSURE RECEPTACLE

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

( * ) Notice: Subject to any disclaimer, the term of this patent is extended or adjusted under 35 U.S.C. 154(b) by 197 days.

(21) Appl. No.: 16/007,306

(22) Filed: Jun. 13, 2018

(65) Prior Publication Data

US 2018/0360515 A1    Dec. 20, 2018

(30) Foreign Application Priority Data

Jun. 14, 2017   (DE) ........................ 10 2017 113 126

(51) Int. Cl.
*A61B 17/88* (2006.01)
*B01F 13/00* (2006.01)
(Continued)

(52) U.S. Cl.
CPC ...... *A61B 17/8825* (2013.01); *A61B 17/8816* (2013.01); *A61B 17/8822* (2013.01);
(Continued)

(58) Field of Classification Search
CPC ............ A61B 17/8825; A61B 17/8816; A61B 17/8822; A61B 17/8805
See application file for complete search history.

(56) References Cited

U.S. PATENT DOCUMENTS 2,446,501 A    8/1948 Weber
4,460,357 A    7/1984 Cohen
(Continued)

FOREIGN PATENT DOCUMENTS

AU    2017258805    5/2018
CN    103318551     9/2013
(Continued)

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).

*Primary Examiner* — Christian A Sevilla
(74) *Attorney, Agent, or Firm* — Dicke, Billig & Czaja, PLLC

(57) ABSTRACT

One aspect relates to a device for producing a bone cement paste from a monomer liquid and a cement powder and for delivering the bone cement paste, the device having a cartridge with a cylindrical interior, the interior of the cartridge being closed at the front side apart from a delivery opening for discharging the bone cement paste from the interior. A delivery plunger is arranged in the interior of the cartridge and mounted so as to be pushable in the direction of the delivery opening. The cement powder is arranged in the interior of the cartridge between the delivery opening and the delivery plunger. A closure closes the delivery opening and is mounted so as to be movable relative to the delivery opening. A line element is arranged at the front side of the delivery opening and includes a closure receptacle for receiving at least part of the closure. The closure is pushable into the closure receptacle by pressure on the bone cement paste such that the delivery opening is opened, when the closure has been pushed into the closure receptacle, the line element provides a free line cross-section through which the (Continued)

bone cement paste is pushable out through the delivery opening and out of the device.

27 Claims, 15 Drawing Sheets

(51) Int. Cl.
    *A61M 5/31*     (2006.01)
    *A61M 5/28*     (2006.01)
    *B01F 15/02*     (2006.01)

(52) U.S. Cl.
    CPC ......... *A61B 17/8827* (2013.01); *A61M 5/284* (2013.01); *A61M 5/3145* (2013.01); *B01F 13/002* (2013.01); *B01F 13/0023* (2013.01); *B01F 15/0206* (2013.01); *B01F 15/0237* (2013.01); *B01F 15/0279* (2013.01); *A61B 2017/8838* (2013.01); *A61M 2005/287* (2013.01); *A61M 2005/3132* (2013.01); *A61M 2210/02* (2013.01); *B01F 2215/0029* (2013.01)

(56) References Cited

U.S. PATENT DOCUMENTS

| | | | |
|---|---|---|---|
| 4,479,801 A * | 10/1984 | Cohen | A61M 5/286 604/238 |
| 4,671,263 A | 6/1987 | Draenert | |
| 4,758,096 A | 7/1988 | Gunnarsson | |
| 4,973,168 A | 11/1990 | Chan | |
| 5,100,241 A | 3/1992 | Chan | |
| 5,344,232 A | 9/1994 | Nelson et al. | |
| 5,586,821 A | 12/1996 | Bonitati et al. | |
| 5,588,745 A | 12/1996 | Tanaka et al. | |
| 5,624,184 A | 4/1997 | Chan | |
| 5,681,317 A * | 10/1997 | Caldarise | A61B 17/8825 604/218 |
| 5,997,544 A | 12/1999 | Nies et al. | |
| 6,033,105 A | 3/2000 | Barker et al. | |
| 6,241,734 B1 * | 6/2001 | Scribner | A61B 17/8816 606/93 |
| 6,386,872 B1 | 5/2002 | Mukasa et al. | |
| 6,709,149 B1 | 3/2004 | Tepic | |
| 6,935,541 B1 | 8/2005 | Campbell et al. | |
| 9,827,030 B2 | 11/2017 | Vogt et al. | |
| 9,901,380 B2 | 2/2018 | Vogt | |
| 10,010,362 B2 | 7/2018 | Vogt et al. | |
| 2004/0074927 A1 | 4/2004 | Lafond | |
| 2004/0260303 A1 * | 12/2004 | Carrison | A61B 17/3472 606/92 |
| 2008/0195082 A1 | 8/2008 | Pauser et al. | |
| 2009/0247664 A1 * | 10/2009 | Truckai | A61B 17/8836 523/116 |
| 2011/0027751 A1 | 2/2011 | Kojima et al. | |
| 2011/0056984 A1 | 3/2011 | Cheetham | |
| 2011/0056985 A1 | 3/2011 | Bublewitz et al. | |
| 2015/0073422 A1 * | 3/2015 | Chegini | A61B 17/8819 606/94 |
| 2015/0359579 A1 | 12/2015 | Sasaki et al. | |
| 2018/0132919 A1 | 5/2018 | Vogt et al. | |

FOREIGN PATENT DOCUMENTS

| | | |
|---|---|---|
| DE | 3640279 | 6/1987 |
| DE | 20107507 | 4/2002 |
| DE | 69812726 | 2/2004 |
| DE | 202005010206 | 10/2005 |
| DE | 102009031178 | 9/2010 |
| DE | 102010019220 | 11/2011 |
| DE | 102013226118 | 6/2015 |
| DE | 102014101305 | 8/2015 |
| DE | 102016121607 | 5/2017 |
| EP | 0071288 | 2/1983 |
| EP | 0692229 | 1/1996 |
| EP | 0796653 | 9/1997 |
| EP | 1005901 | 6/2000 |
| EP | 1016452 | 7/2000 |
| EP | 1020167 | 7/2000 |
| EP | 1614403 | 1/2006 |
| EP | 1886647 | 2/2008 |
| EP | 2596873 | 5/2013 |
| JP | 9-10281 | 1/1997 |
| JP | 2002191622 | 7/2002 |
| JP | 2008017995 | 1/2008 |
| JP | 2015526158 | 9/2015 |
| WO | 9426403 | 11/1994 |
| WO | 9967015 | 12/1999 |
| WO | 0023002 | 4/2000 |
| WO | 0035506 | 6/2000 |
| WO | 2011089480 | 7/2011 |
| WO | 2014140304 | 9/2014 |

* cited by examiner

BONE CEMENT APPLICATOR WITH PIPE LINE ELEMENT AND CLOSURE RECEPTACLE

CROSS-REFERENCE TO RELATED APPLICATION

This Utility Patent Application claims priority to Application No. DE 10 2017 113 126.4, filed on Jun. 14, 2017, which is incorporated herein by reference.

BACKGROUND

One aspect relates to a device for producing a bone cement paste from a monomer liquid and a cement powder as parent components of the bone cement paste and for delivering the bone cement paste.

One aspect also relates to a method for producing a bone cement paste, for example, a polymethyl methacrylate bone cement paste, using such a device.

One aspect provides, for example, a device for separate storage of the cement powder and of the monomer liquid of polymethyl methacrylate bone cement, for subsequent mixing of the cement powder with the monomer liquid to form a bone cement paste, and for delivery of the bone cement paste, an automatic closure being arranged for opening the device. The device according to one embodiment is in one embodiment a full-prepacked cementing system.

Polymethyl methacrylate (PMMA) bone cements are attributed to the pioneering work carried out by Sir John Charnley (Charnley, J.: Anchorage of the femoral head prosthesis of the shaft of the femur. J. Bone Joint Surg. 42 (1960) 28-30). The monomer component in general contains the monomer methyl methacrylate and an activator dissolved therein (N,N-dimethyl-p-toluidine). The powder component, also known as cement powder or bone cement powder, includes one or more polymers which are produced on the basis of methyl methacrylate and comonomers, such as styrene, methyl acrylate or similar monomers by polymerization, for example, suspension polymerization, an X-ray opaque material and the initiator dibenzoyl peroxide. Mixing of the powder component with the monomer component results, through swelling of the polymers of the powder component in the methyl methacrylate, in a plastically deformable paste, the bone cement or bone cement paste proper. On mixing of the powder component with the monomer component, the activator N,N-dimethyl-p-toluidine reacts with dibenzoyl peroxide to form free radicals. The free radicals formed initiate free-radical polymerization of the methyl methacrylate. As polymerization of the methyl methacrylate proceeds, the viscosity of the bone cement paste increases, until it solidifies.

PMMA bone cements may be mixed in suitable mixing cups using spatulas by mixing the cement powder with the monomer liquid. This may result in air bubbles being entrapped in the bone cement paste, which may have a negative effect on the mechanical properties of the cured bone cement.

To avoid entrapped air in the bone cement paste, a wide range of vacuum cementing systems have been described, of which the following are stated by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

Patents DE 10 2010 019 220 B4, EP 2 596 873 B1 and DE 10 2013 226 118 B3 and patent application DE 10 2014 101 305 A1 disclose devices for mixing PMMA bone cement from two pasty parent components.

A further development in cementing technology is represented by cementing systems in which both the cement powder and the monomer liquid have already been packed in separate compartments of the mixing devices and are mixed together in the cementing system only immediately before application of the cement. Such closed, full-prepacked mixing devices have been proposed in EP 0 692 229 A1, DE 10 2009 031 178 B3, U.S. Pat. Nos. 5,997,544 A, 6,709,149 B1, DE 698 12 726 T2, EP 0 796 653 A2 and U.S. Pat. No. 5,588,745 A.

Patent DE 10 2009 031 178 B3 discloses a storage and mixing device in the form of a full-prepacked cementing system, in which the parent components needed to produce the bone cement paste have already been stored in the storage and mixing device and may be combined and mixed in the storage and mixing device. The storage and mixing device has a two-part delivery plunger for closing a cement cartridge. In this case, a combination of a gas-permeable sterilization plunger and a gas-impermeable sealing plunger is used.

After mixing of the cement powder with the liquid monomer component, polymethyl methacrylate bone cements are applied as bone cement paste in the as yet uncured, pasty state. When using mixing devices, in the case of powder/liquid cements the bone cement paste is located in a cartridge. When applying such conventional PMMA bone cements, after mixing of the two parent components, the bone cement paste formed is expelled using manually operable expulsion devices. The bone cement paste is pushed out of the cartridge through the movement of a delivery plunger. Delivery plungers conventionally have a diameter of between 30 mm and 40 mm and thus a surface area on the outside, against which a rod (frequently also known as a tappet) of the expulsion device acts during the expulsion process, of 7.0 $cm^2$ to 12.5 $cm^2$. Movement of the delivery plunger is for example, brought about by manually operable, mechanical expulsion devices. These manual expulsion devices normally achieve an expulsion force in the range of around 1.5 kN to 3.5 N.

These simple mechanical expulsion devices for example, use clamping rods for expulsion purposes, these being driven by a manually actuatable trigger lever. Manually driven expulsion devices have been tried and tested for decades throughout the world and constitute the existing state of the art. One advantage of these expulsion devices is that, by way of the manual force to be applied, the medical user gains a feel for the bone cement paste's resistance to penetration into the bone structures (cancellous bone).

When using any of the hitherto known full-prepacked cementing systems, the medical user has to perform a plurality of working steps in a predetermined order on the devices in succession until the bone cement paste is obtained and can be applied. Any mistakes in the working steps may lead to failure of the mixing device and therefore cause disruption to the course of the operation. Costly training of medical users is therefore necessary to avoid user error.

WO 00/35506 A1 proposes a device in which polymethyl methacrylate cement powder is stored in a cartridge, wherein the cement powder fills the entire volume of the cartridge and the interspaces between the particles of the cement powder have a volume which corresponds to the volume of monomer liquid necessary to produce bone cement paste with the cement powder stored in the cartridge. This device is constructed such that, through the action of a vacuum, the monomer liquid is introduced from above into the cartridge, wherein to this end a vacuum is applied to a vacuum port at the bottom of the cartridge. In this way, the monomer liquid is drawn through the cement powder, wherein the air located in the interspaces between the cement powder particles is displaced by the monomer liquid. Thorough mechanical mixing with a stirrer of the cement paste formed is thus dispensed with.

One disadvantage of this system is that cement powders which swell rapidly with the monomer liquid cannot be mixed using this device, because the rapidly swelling cement powder particles form a gel-like barrier once the monomer liquid has penetrated by roughly 1 to 2 cm into the cement powder and prevent migration of the monomer liquid throughout the cement powder. Conventional cement powders additionally suffer from the phenomenon that, due to different surface energies, the cement powder particles are only poorly wetted by methyl methacrylate. The methyl methacrylate thereby penetrates only relatively slowly into the cement powder. Furthermore, the risk cannot be ruled out of the monomer liquid being sucked off via the vacuum port under the action of the vacuum once the cement powder has penetrated fully through the monomer liquid. Insufficient monomer liquid is then available for curing by free-radical polymerization or the mixing ratio is modified undesirably and thus also the consistency of the bone cement paste. It is moreover a problem that the air enclosed between the cement powder particles has to be displaced from the top downwards through the monomer liquid, because the air, which is of a lower specific weight than the monomer liquid, has the tendency, due to gravity, to migrate upwards in the cement powder and not to migrate downwards in the direction of the vacuum port.

Electrically driven expulsion devices are also known from the field of adhesives and sealants. These devices may be driven both with primary and secondary cells and also by means of a stationary power supply. With their sometimes very significant expulsion forces, these devices may expel particularly viscous, pasty compositions. One disadvantage of the use of electric motors, however, is that they contain non-ferrous metals and are costly to purchase. In the operating area, which must be kept sterile, such devices have to undergo complex sterilization or even be replaced. Electrical wiring may impede movement of the user while operating.

Pneumatic devices have moreover also been proposed. These apparatuses require a stationary or mobile compressed air connection (U.S. Pat. No. 2,446,501 A, DE 20 2005 010 206 U1). To this end, compressed air hoses are needed, which may impede the user's movement.

It is alternatively also possible to use compressed gas cartridges to provide compressed gas. To this end, devices have been proposed in which the compressed gas inflow is controlled by one valve, with the flow of viscous composition being additionally controlled by a second valve (US 2004/0074927 A1, U.S. Pat. No. 6,935,541 B1). In the case of these devices, the gas cartridges are integrated into the devices. In such systems connected to compressed air or containing compressed gas cartridges, a compressed gas source is always necessary, the systems no longer being usable without such a source.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
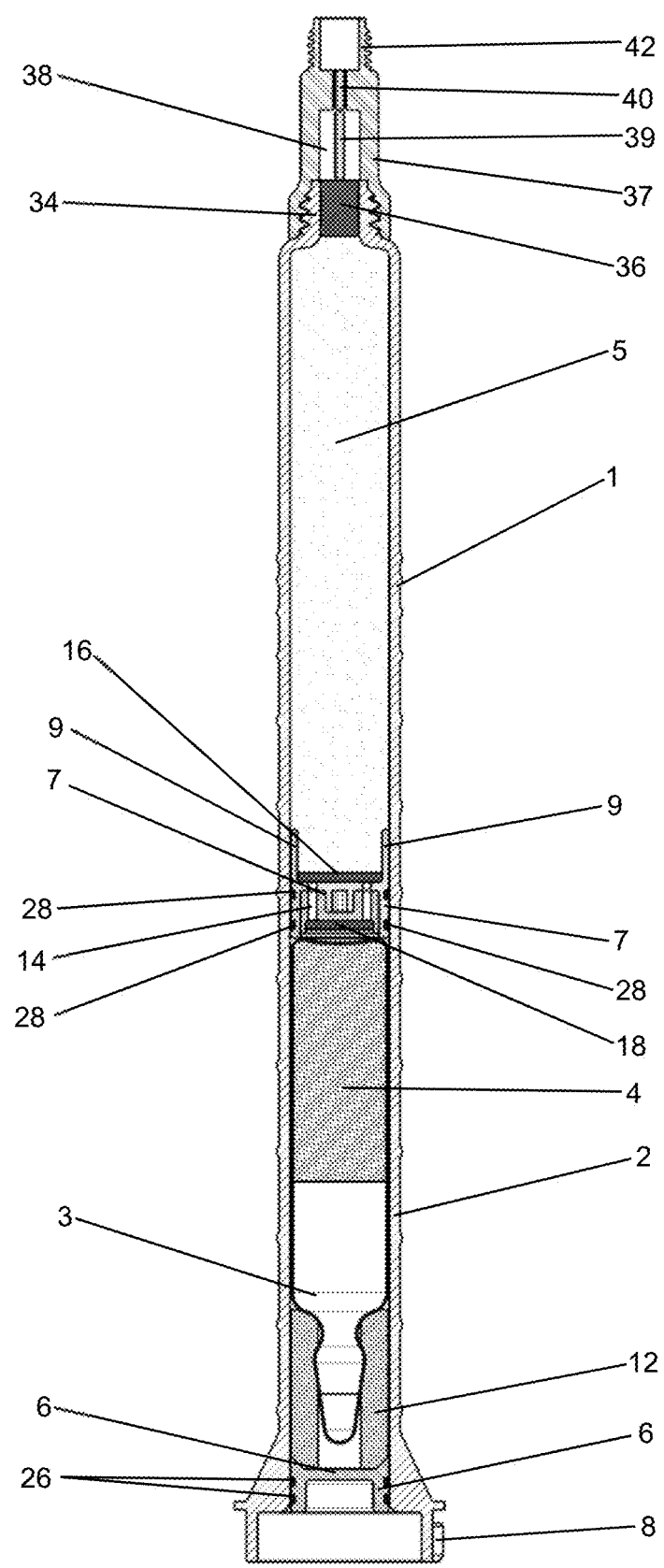
FIG. 1 illustrates a schematic cross-sectional view of a first exemplary device according to one embodiment for storing and mixing a monomer liquid and a cement powder.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

DE 10 2016 121 607, which is not a prior publication, proposes a full-prepacked cementing system with a cartridge containing a bone cement powder. A delivery plunger is provided in the cartridge and behind the cartridge a monomer receptacle is arranged containing a monomer liquid container. At the back side of the monomer receptacle there is located a conveying plunger, with which the monomer liquid container may be crushed and the monomer liquid may be pressed out of the monomer receptacle into the cartridge.

Practical tests have illustrated that the bone cement paste produced using this device always has a good consistency if a suitable cement powder and a suitable ratio by weight of cement powder to monomer liquid are used. If the burst monomer liquid container is maximally compressed during monomer transfer, then a good cement paste is reproducibly obtained. However, the user has in the meantime to remove the device from the expulsion device in order to open the cartridge. The device has then to be reconnected to the expulsion device. It would be for the user if he or she had to connect the device only once to the expulsion device.

Certain combinations may lead to an undesirable change in the consistency of the bone cement paste at the end of the expulsion process, the mixing ratio between the cement powder and the monomer liquid having been changed. In the volumetric range of a few microliters, one to a few small monomer bubbles may however also sometimes occur at the edge of the expelled cement paste.

For the purposes of one embodiment, it has been found that this is associated with the selection and stability of the monomer liquid container and with the penetration of the monomer liquid between the cement powder and the internal wall of the cartridge. Under incomplete compression of the burst monomer liquid container, which may arise for example through selection of a monomer liquid container with very robust walls, a remnant of the monomer liquid may namely remain between the delivery plunger and the conveying plunger within the fragments of the burst monomer liquid container, which remnant may exit through the delivery pipe at the end of expulsion of the bone cement paste through subsequent continued compression of the burst monomer liquid container as a result of axial movement of the conveying plunger towards the delivery plunger. The monomer liquid may creep between the cement powder and the internal wall of the cartridge along the internal wall of the cartridge, without mixing quickly together with surrounding cement powder in the process.

One embodiment thus consists in overcoming the prior art. For example, one embodiment consists in developing a device for storing and mixing the parent components of polymethyl methacrylate bone cement and improving it to the effect that the medical user has only to connect the device with the expulsion device, then by repeated manual actuation of the expulsion device the monomer liquid is mixed with the cement powder and the bone cement paste formed is expelled by subsequent actuation of the expulsion device without additional assembly or disassembly steps being needed for the medical user to open the device. Handling of the device is then very simple, having just one assembly step, compared with cementing systems which are currently commercially available. It is therefore the object to improve the device described in DE 10 2016 121 607, which is not a prior publication, in such a way that formation of the bone cement paste is reproducibly possible, without the device having to be separated from the expulsion device and reconnected thereto.

Furthermore, the device is intended to be provided and suitable for mixing the bone cement paste from the parent components and delivering the mixed bone cement paste. One embodiment is also intended to provide a method for producing a bone cement paste, for example, a polymethyl methacrylate bone cement paste, wherein the bone cement paste is produced from a cement powder and a monomer liquid using such a device, the method overcoming the disadvantages of the prior devices and methods. It is in this respect also an object of one embodiment to prevent the formation of monomer bubbles in the bone cement paste produced. Furthermore, the object of one embodiment is to improve such a device in such a way that the monomer liquid is actively prevented from exiting from the delivery pipe of the cartridge at the end of delivery of the bone cement paste even in the event of incomplete compression of the monomer liquid container. With the device according to one embodiment and the method according to one embodiment it is thus intended to ensure that, even with a very simple and inexpensive device structure and at the same time with very simple and uncomplicated device usability from start to finish of the expulsion process, a homogeneous bone cement paste may be produced and applied.

The device is intended to be drivable by a simple expulsion device and in the process to be as simple as possible to operate. The structure is intended to be inexpensive, and thus the device can only be used once for reasons of hygiene. Many or all of the processes proceeding in the device, such as mixing of the parent components, delivery of the bone cement paste and optionally also opening of the monomer liquid container, and optionally also opening of the cartridge, are intended to proceed with the smallest possible number of working steps and as far as possible automatically and in one embodiment to be driven with a single linear drive.

The object of one embodiment thus also consists in the development of a device for mixing cement powder and monomer liquid. Handling of the device is intended to be maximally simplified, in order to fundamentally avoid user error as a result of incorrectly performed assembly steps. The intention is for a medical user to connect the device to an expulsion device after removal from packaging and then to actuate the latter device. It is intended to avoid further assembly and working steps by the structure of the device. The device is intended in one embodiment also to enable safe storage of cement powder and monomer liquid in mutually isolated compartments, so as to rule out unintentional mixing of the cement components during storage of the device. The device is intended to allow sterilization with the gas ethylene oxide. To this end, the cement powder stored in the device must be accessible to ethylene oxide.

The device is intended to be activatable by means of an expulsion device driven manually during surgery, such that, after interlocking or frictional connection of the device to the expulsion device, through actuation of the expulsion device the axially advanceable rod of the expulsion device acts on the device, optionally opens the monomer liquid container and then, on further movement of the rod, transfers the monomer liquid into the cement powder. Mixing of the monomer liquid with the cement powder is intended to proceed without a mixer movable manually from outside. It is intended, as far as possible, for mixing of the cement components with formation of the bone cement paste, opening of the delivery opening and expulsion of the bone cement paste to proceed only with the forward movement of the rod of the expulsion device. It is in one embodiment also intended for opening of the monomer liquid container and subsequent monomer liquid transfer into the cement powder to proceed as far as possible only with the forward movement of the rod of the expulsion device.

The objects of one embodiment are achieved by a device for producing a bone cement paste from a monomer liquid and a cement powder as parent components of the bone cement paste and for delivering the bone cement paste, the device having a cartridge with a cylindrical interior, in which the parent components are mixable, the interior of the cartridge being closed at a front side apart from a delivery opening for discharging the bone cement paste from the interior, a delivery plunger, which is arranged in the interior of the cartridge and which is mounted so as to be pushable in the direction of the delivery opening, the cement powder, which is arranged in the interior of the cartridge between the delivery opening and the delivery plunger, a closure, which closes the delivery opening and which is mounted so as to be movable relative to the delivery opening, and a line element, which is arranged at a front side of the delivery opening, wherein the line element includes a closure receptacle for receiving at least a part of the closure, wherein the closure is pushable into the closure receptacle by pressure on the bone cement paste, in such a way that the delivery opening is opened, wherein, when the closure has been pushed into the closure receptacle, the line element provides a free line cross-section through which the bone cement paste is pushable out through the delivery opening and out of the device.

For the purposes of one embodiment, the bone cement paste is understood to be bone cement paste even when the parent components have not as yet been completely intermixed, being designated bone cement paste rather once the monomer liquid and the cement powder have been mixed together directly after introduction of the monomer liquid into the cement powder.

The statements of direction made for the purposes of one embodiment relate to the direction of flow of the bone cement paste or to the application opening of the device, wherein the application opening is arranged or defined at the front of the device. The delivery plunger is thus driven from behind and moved forwards in the direction of the delivery opening and in the process the bone cement paste is pushed (or pressed) in the direction of the front side through the delivery opening and through the free line cross-section of the line element, and pushed (or pressed) out of the application opening.

The interior of the cartridge has a cylindrical geometry. The cylindrical shape is the simplest with which the interior of the cartridge may be made. A cylindrical shape should be understood geometrically to mean the shape of a general cylinder with any desired base area, that is, not just a cylinder with a circular base area. The internal wall of the interior of the cartridge may thus be formed by the cylinder envelope of a cylinder with any desired base area, for example, with different base areas, that is, also with base areas which are not circular or round. According to one embodiment, however, a cylindrical geometry with a rotationally symmetrical and for example, circular base area is preferred in one embodiment for the interior (and also for the closure), since this is the easiest to manufacture.

The cartridge, the delivery plunger, the line element and the closure are in one embodiment made from a thermoplastic, for example, using an injection molding method.

With one embodiment it may also be provided that the bone cement paste flows around the closure in the closure receptacle when the bone cement paste flows through the line element, in one embodiment the bone cement paste flows along at least one side face or circumferential surface of the closure past the closure.

The fact that the bone cement paste flows around the closure in the closure receptacle means that the bone cement paste flows in the longitudinal direction of the closure past the closure.

In this way, it is achieved that the construction may be kept very simple, since no additional channels have to be provided through which the bone cement paste flows around the closure in the line means. In addition, the bone cement paste is pushed in the direction of movement of the closure, such that the force which is transferred with the bone cement paste and which is used to provide the flow of bone cement paste does not have to be diverted, whereby the force needed to open the device and to discharge the bone cement paste may be kept low.

It may furthermore be provided that the free line cross-section is delimited on one side at least in areas by the closure, in one embodiment by a side face or a circumferential surface of the closure.

In this way, it is also achieved that the bone cement paste may be pushed in the direction of movement of the closure, that is, so as to flow through the line element, such that the force which is transferred with the bone cement paste and which is used to provide the flow of bone cement paste does not have to be diverted, whereby the force needed to open the device and to discharge the bone cement paste may be kept low.

It may moreover also be provided that the closure becomes firmly lodged in the closure receptacle when it has been pushed out of the delivery opening into the closure receptacle.

This prevents the closure from moving in the closure receptacle when arranged in the flowing bone cement paste. This prevents a change in the flow resistance of the bone cement paste and a change over time in the volumetric flow rate of the bone cement paste.

To simplify the structure, it may be provided that the closure is cylindrical at least in parts, for example, is completely cylindrical, and the closure receptacle forms a hollow-cylindrical sleeve, wherein at least one channel is in one embodiment provided in the circumferential surface of the hollow-cylindrical sleeve, wherein the at least one channel provides the free line cross-section.

This embodiment is particularly easily manufacturable. In addition, the closure may be moved in the axial direction of its cylindrical geometry, such that the movement may be guided particularly easily.

In this respect, it may be provided that the internal diameter of the hollow-cylindrical sleeve is greater than the external diameter of the closure, in one embodiment is at least 1 mm greater than the external diameter of the closure, in one embodiment is between 1 mm and 10 mm greater than the external diameter of the closure.

The resultant free line cross-sections are arranged in such a way or are of such a size that they only slightly impede the flow of the bone cement paste.

It may furthermore be provided that the axial length of the interior of the hollow-cylindrical sleeve is greater than the axial length of the closure, in one embodiment is at least 1 mm greater than the axial length of the closure, in one embodiment is between 1 mm and 20 mm greater than the axial length of the closure.

The closure can thereby be sunk in the sleeve and the bone cement paste may easily flow around the closure.

According to one embodiment, it may be provided that spacers are provided in the closure receptacle for spacing the closure from the internal wall of the closure receptacle, wherein the spacers are in one embodiment bars which are in one embodiment oriented in the direction of movement of the closure and/or are oriented in the direction of flow of the bone cement paste.

In this way, it is ensured that the free line cross-section is achieved by spacing the closure from the internal wall of the closure receptacle when the closure has been pushed into the closure receptacle.

To this end, it may also in one embodiment be provided that the spacers exhibit a height which corresponds to at least one third of the cross-section of the closure, in one embodiment corresponds to at least half the cross-section of the closure. In this way, sufficiently large free line cross-sections are achieved.

It may furthermore also be provided that the free line cross-section is at least half as large as the cross-section of the delivery opening, in one embodiment at least as large as the cross-section of the delivery opening.

In this way, it is achieved that the flow resistance for the bone cement paste is not impaired by too small a free line cross-section of the line element and at the same time the structure of the device is compact.

One embodiment proposes that the length of the closure be greater in the direction of movement thereof than the width in the directions perpendicular thereto.

The direction of movement of the closure in one embodiment corresponds to the longitudinal direction perpendicular to the delivery opening. In this way, the risk may be reduced of the closure becoming wedged on movement into the closure receptacle.

It may in one embodiment also be provided that a limit stop for limiting movement of the closure is arranged in the closure receptacle at a front end wall of the closure receptacle which is remote from the delivery opening, wherein the limit stop spaces the closure, when fully pushed in, from the front end wall at the front side of the closure receptacle, such that the free line cross-section remains between the front side of the closure and the front end wall.

It is thus achieved that the bone cement paste may be passed on or may flow behind the line element in the same direction in which it flowed on pushing in of the closure into the closure receptacle.

Furthermore, one embodiment may be provided for the present device which is also suitable for storing the monomer liquid and thus provides a full-prepacked system.

Furthermore, in one embodiment, which is also suitable for storing the monomer liquid and thus provides a full-prepacked system, it may be provided the device having a monomer receptacle in which the monomer liquid, for example, a monomer liquid container containing the monomer liquid, is contained, wherein a back side of the cartridge is connected with a front side of the monomer receptacle, in one embodiment connected in such a way that the interior of the cartridge is aligned with the interior of the monomer receptacle.

In this way, the device is also suitable for storing the monomer liquid and for mixing the monomer liquid with the cement powder within the device. The device is thus a full-prepacked cementing system. As a result of the aligned interiors of the cartridge and the monomer receptacle, it may be ensured that firstly the conveying plunger may be moved by a pressure acting on the back side of the conveying plunger and then the conveying plunger may be used to drive the delivery plunger by pushing the conveying plunger together with the delivery plunger further in the direction of the delivery opening.

The monomer receptacle is in one embodiment made from a thermoplastic, for example, using an injection molding method. In this way, the device may be manufactured inexpensively as a hygienic disposable product.

In devices according to one embodiment in which the monomer liquid is arranged in a monomer liquid container within the device, it may be provided that the monomer liquid container is a glass ampoule, a plastic ampoule, a plastic film pouch or an aluminum/plastic composite pouch. Such monomer liquid containers may store the monomer liquid for a particularly long time.

In devices according to one embodiment with monomer receptacles it may also be provided that an interior of the monomer receptacle and the interior of the cartridge are connected together via a connection which is permeable to the monomer liquid and gases but impermeable to the cement powder.

In this way, it is ensured that the cement powder does not penetrate through the connection into the interior of the monomer receptacle, there react prematurely with the monomer liquid and then prevent monomer transfer into the interior of the cartridge. The connection is in one embodiment arranged in the delivery plunger.

It may further be provided that the monomer receptacle has a cylindrical interior in which the monomer liquid, for example, a monomer liquid container containing the monomer liquid, is arranged.

The interior of the monomer receptacle has a cylindrical geometry. Here too, the cylindrical shape is the simplest with which the interior of the receptacle may be made. A cylindrical shape should be understood geometrically to mean the shape of a general cylinder with any desired base area, that is, not just a cylinder with a circular base area.

It may furthermore in one embodiment be provided that a conveying plunger movable in the longitudinal direction of the monomer receptacle is arranged in the monomer receptacle, which conveying plunger is advanceable from a back side of the monomer receptacle in the direction of the front side, wherein the monomer liquid, for example, a monomer liquid container containing the monomer liquid, is arranged between the conveying plunger and the delivery plunger.

In this way, a full-prepacked cementing system is provided in which all the parent components of the bone cement paste, namely the monomer liquid and the cement powder, are contained and may also be stored.

The conveying plunger closes the monomer receptacle off liquid-tightly at the back side thereof, apart from any ventilation openings that may be present (see below).

It may in this case be provided that at least one protruding point, edge and/or cutting edge is arranged on the front side of the conveying plunger to break the monomer liquid container.

By applying a defined force at a predetermined, spatially delimited location, the pressure at this location may be increased under identical force and in this way defined breaking of the monomer liquid container may be achieved. In this way, the operation of breaking open the monomer liquid container is more reproducible.

In devices according to one embodiment with conveying plungers, it may alternatively or additionally be provided that the monomer liquid container inside the monomer receptacle is to be opened, in one embodiment broken open or torn open, by a movement of the conveying plunger in the direction of the front side of the monomer receptacle.

In this way, it is achieved that the monomer liquid container may be opened by the axial linear movement of the conveying plunger. An expulsion device with just one rod as axial linear drive may thereby be used both to open the monomer liquid container and to press the monomer liquid into the cartridge and also to press the bone cement paste out of the cartridge.

It may also be provided that at least one ventilation opening, which connects the interior of the monomer receptacle with the surrounding environment, is arranged in the wall of the monomer receptacle.

In this way, the interior of the monomer receptacle may be sterilized with a sterilizing gas.

In this case, it may be provided that the at least one ventilation opening is arranged tightly in the region of the conveying plunger such that it is closed by a movement of the conveying plunger towards the front side of the monomer receptacle before a monomer liquid container arranged in the monomer receptacle, in which monomer liquid container the monomer liquid is contained, is opened by the movement of the conveying plunger.

In this way, the monomer liquid cannot escape from the interior of the monomer receptacle when the at least one ventilation opening is closed by the conveying plunger moving towards the front side of the monomer receptacle before the monomer liquid container is opened by the movement of the conveying plunger, that is, is for example crushed, shattered or torn open by the conveying plunger in the interior of the monomer receptacle.

It may in one embodiment be provided that the monomer receptacle and the cartridge are formed in one piece by a tubular container.

This structure is the simplest and most inexpensive structure achievable.

It may further be provided that a fastening means is arranged on the back side of the device for fastening an expulsion device with which the delivery plunger is pushable in the direction of the delivery opening.

The device may be connected and fastened therewith to an expulsion device with an advanceable rod.

It may be provided that the cement powder rests against the front side of the delivery plunger, for example, over the whole surface thereof, wherein the cement powder is in one embodiment pressed into the interior of the cartridge.

This prevents relatively large amounts of entrapped gas from remaining in the cartridge, which might lead to entrapped gas in the bone cement paste on mixing of the monomer liquid with the cement powder. This cannot happen with a densely packed or in one embodiment pressed cement powder, since the monomer liquid wets the particles of the cement powder well and the surface tension of the monomer liquid then does not allow any or at least no relevant entrapped gas between the particles of the cement powder.

According to a further development of one embodiment, it may be provided that a hollow cylinder is arranged at a front side of the delivery plunger facing the delivery opening, wherein the hollow cylinder is open at its front side facing the delivery opening and in one embodiment extends from the front side of the delivery plunger at least 3 mm into the interior of the cartridge.

With the hollow cylinder at the front side of the delivery plunger, it is possible to guide or to allow the monomer liquid to flow, on pressing into the cement powder in the interior of the cartridge, over a greater distance through the cement powder before the monomer liquid reaches the internal wall of the cartridge. In this way, it possible to prevent or reduce the formation of monomer liquid bubbles or entrapped monomer liquid in the bone cement paste formed, so producing a more homogeneous bone cement paste. It has furthermore been found that it is possible, by retaining in the interior of the cartridge a small remnant of the bone cement paste arising in the cartridge in the form of the mixture of the cement powder with the monomer liquid, for no bone cement paste of a different consistency to be delivered at the end of the expulsion process, since the residual bone cement paste is retained in the cartridge and the delivery opening is closed.

It may in one embodiment be provided that the delivery plunger is tight or sealed relative to the internal wall of the interior of the cartridge, for example, is sealed with at least one circumferential seal.

It may be provided that the delivery opening is arranged in the front side of the cartridge.

The hollow cylinder is arranged in the interior of the cartridge. The front side of the delivery plunger is in one embodiment planar apart from the hollow cylinder.

The fact that the hollow cylinder extends from the delivery plunger in the direction of the front side of the cartridge and thus in the interior of the cartridge means that a dead volume is delimited by the hollow cylinder in the interior of the cartridge. Because a dead volume remains in the interior of the cartridge, a volume may remain between the delivery opening and the delivery plunger which is filled with a bone cement paste of varying composition when the hollow cylinder is pushed against the front side of the interior of the cartridge and the delivery plunger thereby cannot be advanced any further in the direction of the delivery opening.

In devices according to one embodiment, it may be provided that the hollow cylinder is spaced at its external circumferential surface at most by 0.5 mm from the internal wall of the interior of the cartridge, in one embodiment at most 0.1 mm from the internal wall of the interior of the cartridge.

In this way, it is ensured that no or only a little cement powder, which is difficult for the monomer liquid to reach and which would impede movement of the delivery plunger, is located between the internal wall of the interior of the cartridge and the external circumferential surface of the hollow cylinder.

It may also be provided that the hollow cylinder rests at least in areas against the internal wall of the interior of the cartridge, in one embodiment with its external circumferential surface against the internal wall of the interior of the cartridge.

It is thus ensured that no cement powder, which is difficult for the monomer liquid to reach and which would impede movement of the delivery plunger, is located between the internal wall of the interior of the cartridge and the external circumferential surface of the hollow cylinder.

In devices according to one embodiment, it may be provided that the hollow cylinder blocks further movement of the delivery plunger in the direction of the front side of the cartridge when the front side of the hollow cylinder rests against the front side of the interior of the cartridge, such that the delivery plunger is spaced from the front side of the interior of the cartridge and a dead volume remains in the interior of the cartridge.

It is thus achieved that the dead volume enclosed in the hollow cylinder retains in the cartridge a remnant of the bone cement paste produced which is less well mixed or which has a variable consistency due to monomer liquid continuing to flow into the interior of the cartridge at the end of the expulsion process.

It may furthermore be provided that the hollow cylinder has at least one slot, in one embodiment at least one extending parallel to the cylinder axis of the hollow cylinder, in one embodiment at least one slot reaching from the front side to the delivery plunger.

In this way, the fit of the hollow cylinder may be more readily adapted to the internal wall of the cartridge and the risk of movement of the delivery plunger being blocked with the hollow cylinder is reduced. As an alternative to a course parallel to the cylinder axis of the hollow cylinder, the at least one slot may also run in the form of a spiral in the wall of the hollow cylinder.

It may furthermore be provided that at least one connection is provided in the delivery plunger from the back side of the delivery plunger to the front side of the delivery plunger for introducing the monomer liquid into the interior of the cartridge, wherein the at least one connection is permeable to the monomer liquid and gases and impermeable to the cement powder and wherein the at least one connection in one embodiment leads from the delivery plunger inside the hollow cylinder or through lines in the hollow cylinder at the front side of the hollow cylinder into the interior of the cartridge.

In this way, the monomer liquid, when passed through the feed-through and, inside the hollow cylinder, into the cement powder, has firstly to flow through the cement powder inside the hollow cylinder and cannot flow past the cement powder at the internal wall of the cartridge and so arrive at the delivery opening. When the monomer liquid is passed through the lines in the hollow cylinder into the interior of the cartridge, it flows in a region closer to the middle of the interior of the cartridge, such that the monomer liquid may spread from there also in the direction of the delivery plunger and become better distributed. The mouth of the lines leading into the interior of the cartridge is in one embodiment located in the region of the inner circumferential surface of the hollow cylinder. In this way, it is ensured that the monomer liquid cannot flow along the shortest path to the internal wall of the interior of the cartridge. All of these measures serve to ensure that the bone cement paste produced and the bone cement paste delivered from the device is more homogeneous and no or as little as possible of the monomer liquid becomes entrapped in the bone cement paste.

One further development of one embodiment proposes that cement powder is contained, for example, pressed in, in the part of the interior of the cartridge enclosed by the hollow cylinder.

This makes it clear that a dead volume is to be formed for the bone cement paste in the part enclosed by the hollow cylinder and nothing else is located therein.

It may in one embodiment be provided that the part of the interior of the cartridge delimited by the hollow cylinder is at least 1 $cm^3$ in size, in one embodiment at least 3 $cm^3$ in size.

In this way, it is ensured that the enclosed dead volume is sufficiently large to accommodate the residual quantity of bone cement paste of varying consistency arising at the end of the mixing process, without this being able to be delivered and applied using the device. These dead volumes are sufficient to retain in the interior of the cartridge incompletely mixed proportions of the bone cement paste which may arise in the interior of the cartridge in the region of the delivery plunger. It is thereby possible to prevent poorly mixed bone cement paste or a bone cement paste of varying composition and thus consistency, which is unusable, from being delivered at the end of the delivery process.

According to one embodiment, it may be provided that the hollow cylinder extends from the front side of the delivery plunger at least 5 mm into the interior of the cartridge, in one embodiment at least 7.5 mm into the interior of the cartridge, in one embodiment at least 10 mm into the interior of the cartridge.

Thus, on the one hand the dead volume in the region enclosed by the hollow cylinder is increased and on the other hand the distance to the boundary surface between the cement powder and the internal wall of the cartridge is increased which the monomer liquid has to travel through the cement powder before the risk arises of the monomer liquid being able to flow along the internal wall of the cartridge past the cement powder or bone cement paste which has already arisen.

It may furthermore be provided that the wall thickness of the hollow cylinder amounts to at least 1 mm, in one embodiment at least 1.5 mm, and in one embodiment at least 2 mm.

This measure also serves to lengthen the distance traveled by the monomer liquid up to the internal wall of the cartridge and thereby to achieve greater homogeneity of the bone cement paste produced. In addition, in this way sufficient stability of the hollow cylinder in one embodiment consisting of plastic is brought about, such that this is not deformed or not excessively deformed at the end of the expulsion process.

It may also be provided that the closure has an indentation at the back side facing the interior of the cartridge, in which indentation a frontmost part of the cement powder is contained.

In this way, it is achieved that the frontmost part of the bone cement paste, which is contained in the indentation, remains in the closure and is pushed forwards therewith. The remaining bone cement paste then flows around the closure with the portion contained therein. The monomer liquid arrives in this frontmost portion last when pressed in from the back side into the cement powder. The portion of the bone cement paste in the indentation may thus have a different composition from the rest of the bone cement paste. In this way, a less thoroughly mixed part of the bone cement paste may thus be retained in the closure.

The closure in one embodiment forms with the delivery plunger a cartridge closure system openable by axial pressure acting on the delivery plunger in the direction of the delivery opening.

It may moreover be provided that the volume of the closure receptacle is sufficiently large to accommodate at least a part of the closure, wherein the closure receptacle is in one embodiment sufficiently large to accommodate the closure completely and in one embodiment the closure receptacle has a larger volume than the volume of the closure.

In this way, it may be ensured that the closure, when in the displaced and thereby open position, does not stand in the way of the flow of the bone cement paste and thereby impede expulsion of the bone cement paste.

The objects addressed by present embodiments are also achieved by a method for producing a bone cement paste, for example, a polymethyl methacrylate bone cement paste, wherein the bone cement paste is produced from a cement powder and a monomer liquid using a device according to one embodiment, characterized by the following succession of steps:
a) the monomer liquid is pushed into the interior of the cartridge, such that the monomer liquid mixes with the cement powder and there forms the bone cement paste,
b) the bone cement paste is pushed with the delivery plunger in the direction of a front side of the cartridge,
c) the closure is pushed into the closure receptacle by the pressure of the bone cement paste acting on the closure and the delivery opening is opened in the process,
d) the bone cement paste flows through the line element through the free line cross-section and is delivered from the device.

In this respect, it may be provided that the device is inserted into an expulsion device prior to step a), the expulsion device having an axially advanceable rod, wherein the delivery plunger is in one embodiment advanced with the rod in the direction of the delivery opening of the cartridge.

This enables use of a simple device due to the application of a conventional commercial expulsion device.

It may on the other hand be provided that, after insertion of the device into the expulsion device, a conveying plunger, which is mounted movably inside a monomer receptacle arranged on the back side of the cartridge at the back side of the monomer receptacle, is advanced with the rod in the direction of the cartridge, wherein through movement of the conveying plunger a monomer liquid container, in which the monomer liquid is contained, is opened and the monomer liquid is pressed out of the monomer receptacle into the cartridge, wherein the cement powder mixes with the monomer liquid in the interior of the cartridge to yield the bone cement paste.

This enables the device to be used as a full-prepacked mixing system.

It may also be provided that a hollow cylinder is arranged at a front side of the delivery plunger facing the delivery opening, wherein the monomer liquid flows around the hollow cylinder before arriving at the internal wall of the cartridge and/or the delivery plunger meets with a front side of the cartridge, wherein further movement of the delivery plunger in the direction of the delivery opening is blocked with the hollow cylinder and a residual quantity of the bone cement paste remains in the part of the interior of the cartridge delimited by the hollow cylinder.

Using the hollow cylinder ensures that at the end of the expulsion process a less well mixed remainder of the bone cement paste or a part of the bone cement paste which is of a different composition is retained in the cartridge and not used for application.

Finally, it may also be provided that in step a) the monomer liquid is pressed through at least one connection in the delivery plunger impermeable to the cement powder but permeable to gases and the monomer liquid into the cartridge, in one embodiment is pressed into the cartridge by movement of a conveying plunger which is driven with the rod of the expulsion device.

This prevents the monomer liquid from mixing prematurely with the cement powder.

One embodiment is based on the surprising recognition that it is possible, with the closure sinkable in the closure receptacle and the free cross-section in the line cross-section, to enable opening of the cartridge inside the device without the closure having to be removed or falling out of the device.

To this end, a maximally simple closure system has been developed, in which the closure of the device opens automatically through movement of the bone cement paste formed or by a linear pressure exerted on the bone cement paste. The closure or closure body does not in the process fall off or out of the device after opening of the device. The closure system is made such that the cement powder is securely enclosed, and the closure only opens when bone cement paste has been formed by mixing the monomer liquid with the cement powder. The cement powder namely does not pass a pressure exerted on the delivery plunger on to the closure, since the powder particles rest against the side walls of the cartridge if they have not been mixed with the monomer liquid. The closure system is designed such that it is a component part of the device and the closure is fitted in such a way that tampering from outside is possible only with difficulty.

The device according to one embodiment, in its further development as a full-prepacked cementing system, has the significant advantages that the two parent components of the bone cement paste are stored in the closed cementing system and that mixing of the parent components proceeds in the closed device. This means that the device does not have to be filled by the user. The medical user has no contact with the individual parent components of the bone cement. Odor nuisance thereby remains minimal. A particular advantage of the device also consists in the fact that the monomer liquid is pressed into the cement powder simply by moving forwards a rod of a manually driven expulsion device. In the process, the air present between the cement powder particles is displaced by the monomer liquid. A homogeneous bone cement paste arises without any need for manual mixing with mixing rods with mixing blades. This means that error-prone manual mixing is no longer necessary. Operation of the device is simplified to the greatest possible extent. The system is a ready-to-use system.

The advantages of devices and methods according to one embodiment are based fundamentally on the fact that the per se known linear forward movement of rods of manually operated expulsion devices is exploited in such a way that, through continuous action of the force of the linear forward movement of the rod, firstly a monomer liquid container is opened, the monomer liquid container is then compressed, whereby the monomer liquid exits from the monomer liquid container and is pressed into compacted cement powder, wherein the air present between the cement powder particles is displaced by the pressed-in monomer liquid and, after wetting of the cement powder particles by the monomer liquid, a bone cement paste arises. A prerequisite for this is the use of a cement powder which is such that it is very readily wetted by the monomer liquid and can suck up the latter by capillary action.

The device may be used as a hygienic disposable product, since it may be manufactured to a very considerable extent of plastic and because all parts including the interiors and the cement powder are sterilizable by means of ethylene oxide.

An example of a device according to one embodiment for storing, mixing and delivering polymethyl methacrylate bone cement may for example have:
a) a hollow-cylindrical container which forms a cartridge at the front and a monomer receptacle at the back, wherein the container has an element arranged at the rear end for connection with an expulsion device,
b) a cartridge head, which terminates the hollow-cylindrical cartridge, wherein a feedthrough for accommodating the delivery pipe is arranged in the cartridge head, and wherein at least one feedthrough connects the outside of the cartridge head gas-permeably with the inside of the cartridge head,
c) a delivery pipe,
d) a sterilization plunger as closure which is axially mobile in the cartridge head and is gas-permeable but impermeable to powder particles,
e) a conveying plunger, which is arranged in an axially mobile manner in the monomer receptacle and which closes the cartridge bottom in a liquid-impermeable manner,
f) a delivery plunger which is axially mobile in the cartridge and which is arranged in the cartridge between the sterilization plunger and the conveying plunger, wherein the delivery plunger has at least one feedthrough between the two end faces which is liquid-permeable and impermeable to powder particles, and wherein a hollow cylinder is arranged on the delivery plunger at the end face pointing towards the cartridge head, the external circumferential surface of which hollow cylinder lies against the internal cartridge wall, wherein the hollow cylinder has a height of at least 3 mm in the axial direction and a wall thickness of at least 1 mm,
g) at least one monomer liquid container in the monomer receptacle, which monomer liquid container contains the monomer liquid,
h) cement powder, which is arranged between the delivery plunger and the cartridge head, wherein
i) a hollow-cylindrical sleeve is arranged as closure receptacle between the delivery pipe and the delivery opening of the cartridge head, wherein the internal diameter of the sleeve is greater than the external diameter of the sterilization plunger, wherein the axial length of the interior of the sleeve is smaller than the axial length of the sterilization plunger, wherein
j) spacers are mounted on the internal wall of the sleeve, wherein the radial distance from the longitudinal axis of the cartridge to the inward-pointing edges of the spacers is greater than or equal to the radius of the sterilization cylinder, and wherein
k) the sterilization plunger is pushed out of the proximal cartridge into the sleeve by axial motion of the bone cement paste, wherein, once the sterilization plunger has been received in the sleeve, the bone cement paste flows around the sterilization cylinder at least in part and then exits the sleeve through a proximal opening.

A method according to one embodiment, having the following successive steps, may for example be implemented using the exemplary device for mixing the cement powder with the monomer liquid, forming bone cement paste:
a) connecting the expulsion device with the connecting element of the hollow-cylindrical container,
b) advancing the rod of the expulsion device,
c) displacing the conveying plunger in the direction of the cartridge head,
d) compressing the at least one monomer liquid container between the delivery plunger and the conveying plunger,
e) bursting or tearing the monomer liquid container,
f) pushing together the burst or torn monomer liquid container and expelling the air from the interior of the monomer receptacle and the monomer liquid with the conveying plunger through the at least one connection of the delivery plunger into the cement powder in the interior of the cartridge,
g) pushing the monomer liquid container further together and expelling the monomer liquid with the conveying plunger through the liquid-permeable connection in the delivery plunger and introducing the monomer liquid through the hollow cylinder into the cement powder in the interior of the cartridge,
h) dispersing the monomer liquid in the cement powder with simultaneous displacement of the air out of the interspaces between the cement powder particles,
i) wetting the cement powder particles with the monomer liquid,
j) venting the air out of the cement powder through the gas-permeable closure,
k) swelling of the cement powder particles by the monomer liquid and initiation of free-radical polymerization of the monomer liquid by reaction of the accelerator with the initiator,
l) forming the bone cement paste from the cement powder and the monomer liquid,
m) displacing the sterilization plunger into the sleeve by axial application of pressure by the bone cement paste pressed axially in the direction of the cartridge head,
n) terminating the proximal movement of the sterilization plunger by the limit stop in the sleeve,
o) the bone cement paste flowing around the sterilization plunger as a result of the forwards motion of the conveying plunger and of the delivery plunger.

Further exemplary embodiments are explained below with reference to fifteen schematically depicted figures, but without thereby restricting the embodiments.

FIGS. 1 to 9 illustrate illustrations of a first device according to one embodiment. FIGS. 1 to 3 and 5 illustrate different schematic overall views of the exemplary device according to one embodiment. FIGS. 4 and 6 to 9 illustrate schematic cross-sectional views as detail views, in the form of enlarged details, through different regions of the first device according to one embodiment.

The first device according to one embodiment consists substantially of a tubular container of plastic, which forms as the front part (at the top in FIGS. 1 and 2, to the left in FIGS. 3, 4 and 7 to 8, top right in FIG. 5, bottom left in FIG. 6, to the left in the two right-hand illustrations of FIG. 9 and in the viewing plane in the two left-hand illustrations of FIG. 9) a cartridge 1 with a cylindrical interior and which forms as the rear part a monomer receptacle 2 for a glass ampoule 3 as monomer liquid container. Instead of the glass ampoule 3, a break-openable plastic ampoule may also straightforwardly be used or, with minor alterations, a tear-openable film pouch consisting of a metal-coated plastic may also be used instead of the glass ampoule 3.

Figure 2:
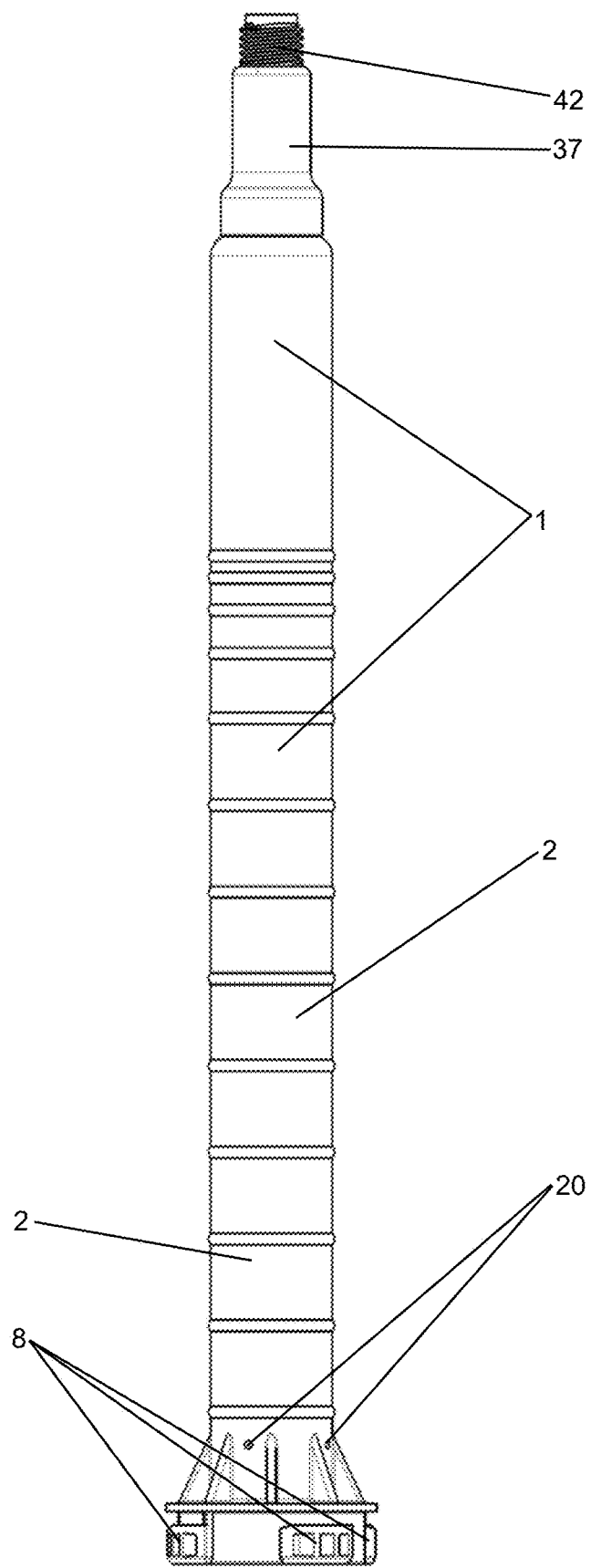
FIG. 2 illustrates a schematic side view of the device according to FIG. 1.
Figure 3:
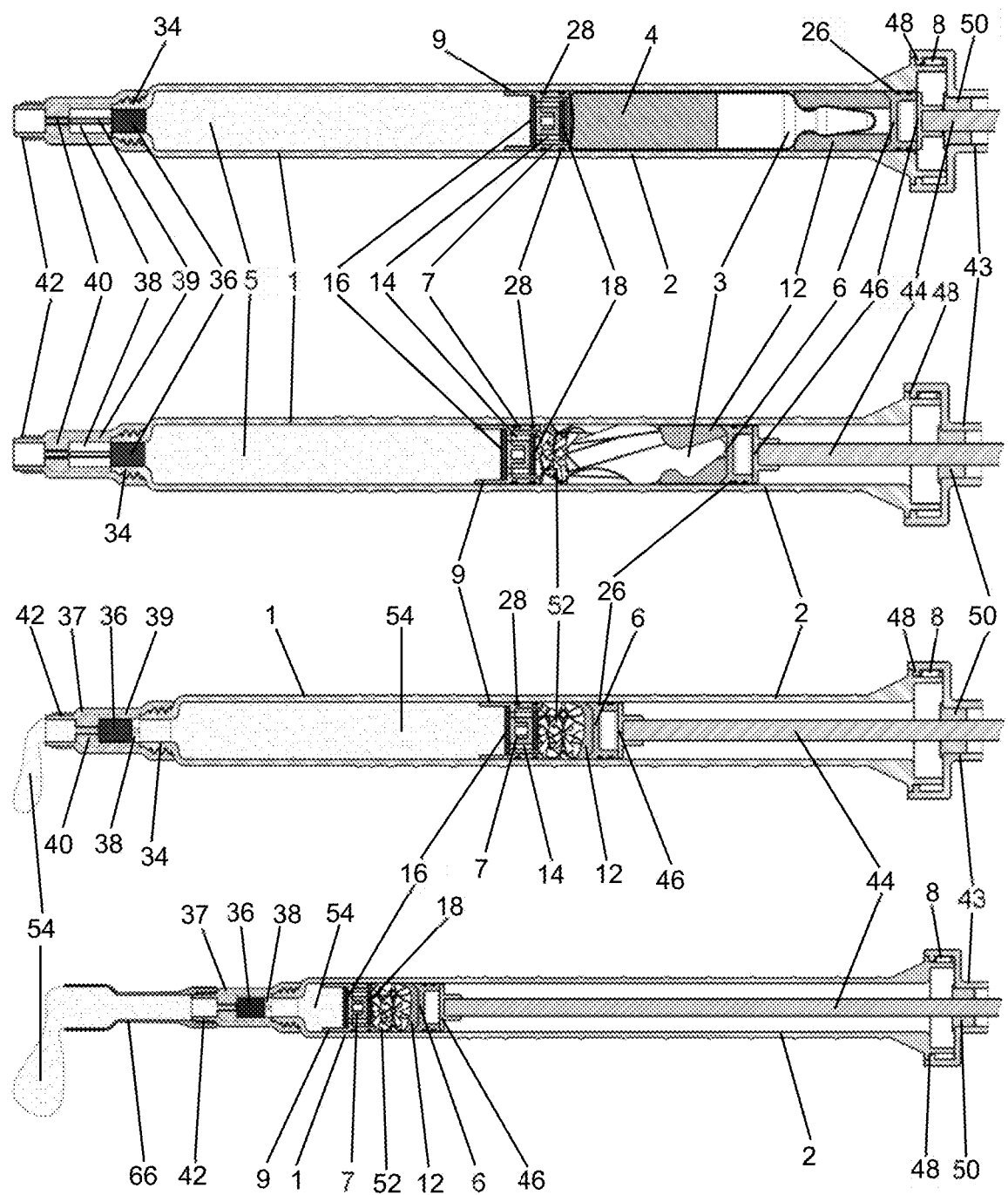
FIG. 3 illustrates four schematic cross-sectional views one above the other of the device according to FIGS. 1 and 2 with a connected expulsion device to illustrate the sequence of a method according to one embodiment.
Figure 5:
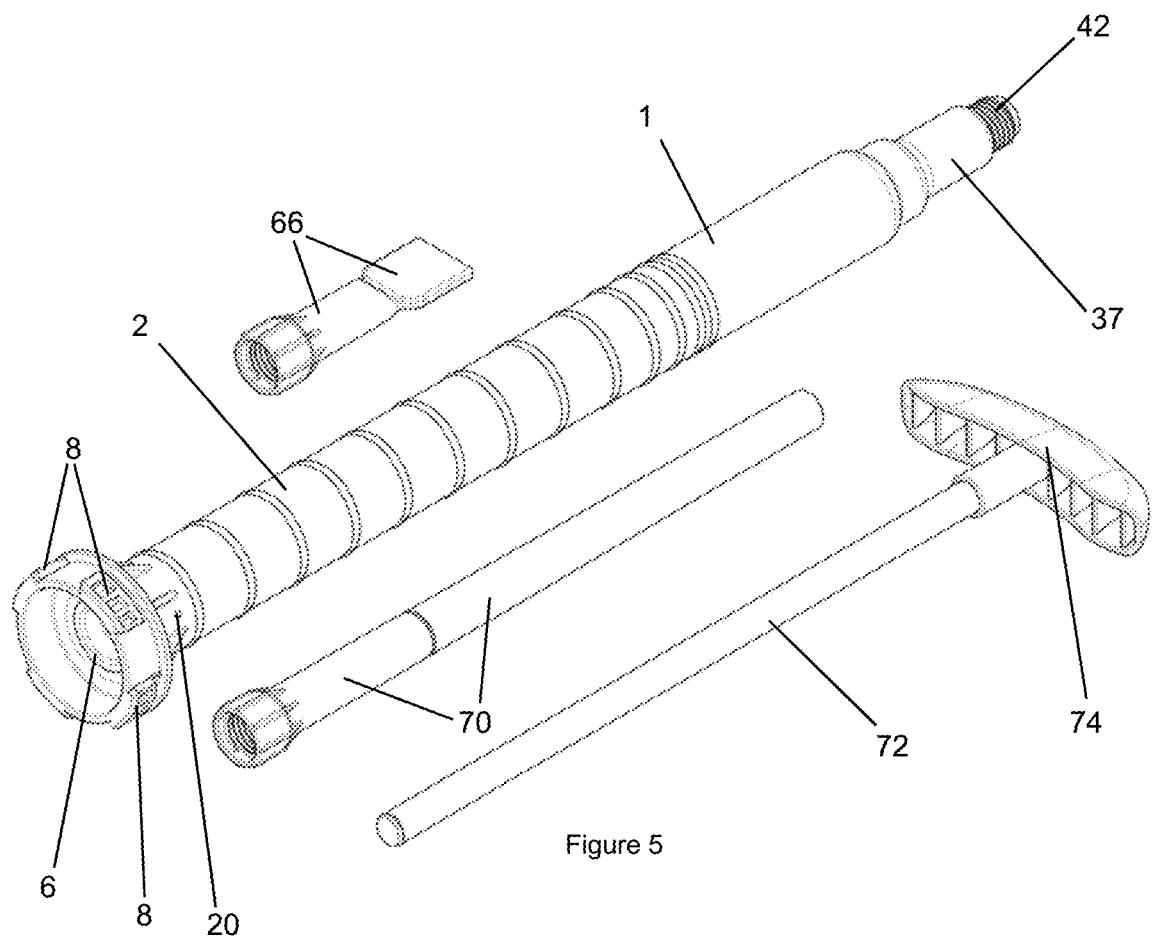
FIG. 5 illustrates a schematic perspective view of the parts of a device according to one embodiment with application tube and a delivery pipe extension.

The back side of the device is illustrated at the bottom in FIGS. 1 and 2, to the right in the illustrations of FIG. 3 and bottom left in FIG. 5. The tubular shape of the container is particularly apparent in the cross-sectional views of FIGS. 1 and 3 and the perspective view according to FIG. 5. Both the interior of the cartridge 1 and the interior of the monomer receptacle 2 are cylindrical with a circular base area. In this respect, the diameter of the interior of the cartridge 1 and the diameter of the interior of the monomer receptacle 2 are identical in size and aligned. The container with the monomer receptacle 2 and the cartridge 1 is in one embodiment produced from plastic using injection molding technology. The monomer receptacle 2 thus has a cylindrical interior, into which the glass ampoule 3 has been placed. The glass ampoule 3 contains the monomer liquid 4. In FIG. 1 the device is illustrated turned upside-down, such that gravity works upwards and the monomer liquid 4 collects in the upper part of the glass ampoule 3. A cement powder 5 has been poured or in one embodiment pressed into the interior of the cartridge 1. The monomer liquid 4 and the cement powder 5 form the parent components for a PMMA bone cement, which is producible using the device. Owing to the glass ampoule 3, the monomer liquid 4 can be stored for a very long time in the monomer receptacle 2 and thereby in the device. The cement powder 5 can likewise be stored for extended periods in the device. The device is thus suitable for storing the monomer liquid 4 and the cement powder 5 as parent components of a bone cement paste of the PMMA bone cement. The device is, however, also suitable and provided for mixing the bone cement paste from the parent components and for delivering the mixed bone cement paste.

Arranged in the monomer receptacle 2 is a conveying plunger 6 of plastic movable in the longitudinal direction in the cylindrical interior of the monomer receptacle 2. The conveying plunger 6 is arranged in the region of the back side of the monomer receptacle 2. The glass ampoule 3 may be compressed, and shattered in the process, in the monomer receptacle 2 using the conveying plunger 6, in that the conveying plunger 6 is pushed in the direction of the front side, that is, in the direction of the cartridge 1. The conveying plunger 6 has wipers at the front side with which splinters of the glass ampoule 3 are wiped off the internal wall of the monomer receptacle 2. To this end, the wipers rest laterally against the internal wall of the interior of the monomer receptacle 2.

A delivery plunger 7 of plastic is arranged in the interior of the cartridge 1, in the back side thereof (towards the bottom in FIGS. 1 and 2, to the right in FIGS. 3, 4, 7 and 8). At the back side of the monomer receptacle 2 a fastening means 8 is provided, with which the monomer receptacle 2 and/or the container may be connected to an expulsion device 43 (not visible in FIGS. 1 and 2 but see FIG. 3). The fastening means 8 is in one embodiment suitable and provided for forming a bayonet closure 8. The conveying plunger 6, which is freely accessible from the back side of the monomer receptacle 2, can thereby be advanced with the expulsion device 43 in the direction of the front side of the cartridge 1.

At its front side, the delivery plunger 7 has a hollow cylinder 9 for extending the distance over which the monomer liquid 4 must flow through the cement powder 5 until it reaches the internal wall of the cartridge 1. In addition, the hollow cylinder 9 serves to space the delivery plunger 7 from a delivery opening at the front side of the interior of the cartridge 1 and to create a dead volume between the delivery plunger 7 and the front side of the interior of the cartridge 1 when the delivery plunger 7 or the hollow cylinder 9 is pushed to the greatest possible extent against the front side of the interior of the cartridge 1. In the present case, the hollow cylinder 9 is rotationally symmetrical and is shaped in the manner of a tube section. The hollow cylinder 9 may, however, also have longitudinal cuts extending parallel to the cylinder axis of the hollow cylinder 9. At the front side the hollow cylinder 9 is planar.

In the interior of the monomer receptacle 2 a bearing 12 of foam is provided which serves as a transport safeguard and as an impact safeguard for the glass ampoule 3. In this way it is intended to prevent the glass ampoule 3 from breaking open unintentionally in the event of vibrations or impacts. The foam and thus the bearing 12 are gas-permeable.

The cartridge 1 and the monomer receptacle 2 are embodied in one piece as a joint plastics part. The monomer receptacle 2 and the cartridge 1 are connected together via a connection 14 in the delivery plunger 7 in a liquid-permeable manner for the monomer liquid 4. The connection 14 through the delivery plunger 7 leads through a porous filter 16 impermeable to the cement powder 5 but permeable to the monomer liquid 4 into the interior of the cartridge 1.

At the mouth leading to the connection 14 a filter 18 is arranged in the delivery plunger 7, with which filter the splinters of the glass ampoule 3 can be held back. A screen may also be provided instead of the filter 18 or in addition to the filter 18.

A plurality of ventilation openings 20 are provided in the wall of the monomer receptacle 2, through which the interior of the monomer receptacle 2 may be sterilized by means of a sterilizing gas such as ethylene oxide. The bearing 12 is likewise gas-permeable and therefore does not close the ventilation openings 20. The ventilation openings 20 are arranged directly adjacent the conveying plunger 6, such that the conveying plunger 6 is pushed directly in front of the ventilation openings 20 and thus directly closes the ventilation openings 20 when the conveying plunger 6 is advanced in the direction of the cartridge 1. This prevents monomer liquid 4 from being able to escape through the ventilation openings 20 when the glass ampoule 3 in the monomer receptacle 2 has been opened.

The cylindrical conveying plunger 6 has an outer circumference which matches the cylindrical geometry of the interior of the monomer receptacle 2 and is sealed in liquid-tight manner relative to the internal wall of the monomer receptacle 2 via two circumferential seals 26. The delivery plunger 7 is likewise sealed in liquid-tight manner relative to the internal wall of the cartridge 1 via two circumferential seals 28. These seals 26, 28 serve to prevent monomer liquid 4 or bone cement from escaping, so as to prevent contamination of the surrounding environment (the operating room and the user). To this end, the seals 26, 28 may consist of rubber.

The interior of the cartridge 1 leads at the front side into a fitting 34, which defines the delivery opening of the cartridge 1. The fitting 34 has an outer thread. Inside the fitting 34 a closure 36 for the cartridge 1 is arranged, which is lodged in the delivery opening and closes it. The closure 36 is a porous filter impermeable to the cement powder 5 but permeable to gases and has a cylindrical shape.

A line element 37 with a closure receptacle 38 for receiving the closure 36 is fastened to the outer thread of the fitting 34. The closure receptacle 38 is shaped in the manner of a sleeve and has four longitudinally oriented bars 39 extending into the closure receptacle 38. The bars 39 space the closure 36 from the internal wall of the closure receptacle 38 when the closure 36 has been pushed into the closure receptacle 38. The line element 37 narrows in front of the closure receptacle 38. In this region four further bars 40 are arranged, which form a limit stop 40 for movement of the closure 36 and thus limit movement of the closure 36 into the closure receptacle 38. A sufficiently large free line cross-section 76 (see FIGS. 6 and 9) is provided between the bars 39, 40, such that the bone cement paste may flow through between the bars 39, the wall of the closure receptacle 38 and the pushed-in closure 36 and between the bars 40 in the front part of the line element 37. At the front side thereof, the line element 37 terminates in a fitting 42 with an outer thread.

Through the closure 36 embodied as a porous filter, the inside of the cartridge 1 and the cement powder 5 may be sterilized using ethylene oxide, since the line element 37 is open and the closure 36 and the interspaces between the powder particles of the cement powder 5 are air-permeable. At the same time, air may be expelled from the monomer receptacle 2 through the cement powder 5, the closure 36 and the open line element 37 when the conveying plunger 6 is pressed in the direction of the monomer receptacle 1.

The cement powder 5 is enclosed in the cartridge 1, since all the openings and connections 14 are closed in a manner impermeable to the cement powder 5 by means of the porous filters 16, 36. The contents of the cartridge 1 may in this respect be sterilized by evacuation and flushing with ethylene oxide. This renders the device also suitable for long-term storage of the cement powder 5.

FIG. 5 illustrates not only the device but also an application tube 66 and a delivery pipe extension 70 for the device, which are two alternatives which may each be screwed onto the fitting 42 of the line element 37. To this end, the application tube 66 and the delivery pipe extension 70 have an inner thread matching the outer thread of the fitting 42 of the line element 37. The delivery pipe extension 70 may be closed with a closure 72. The closure 72 ends in a handle 74, with which the delivery pipe extension 70 may be readily screwed by hand onto the line element 37 when the closure 72 is lodged in the delivery pipe extension 70. In addition, the handle 74 may be used readily to remove the closure 72, which closes the side of the delivery pipe extension 70 facing the cartridge 1, even if the delivery pipe extension 70 is firmly screwed together with the line element 37.

Figure 6:
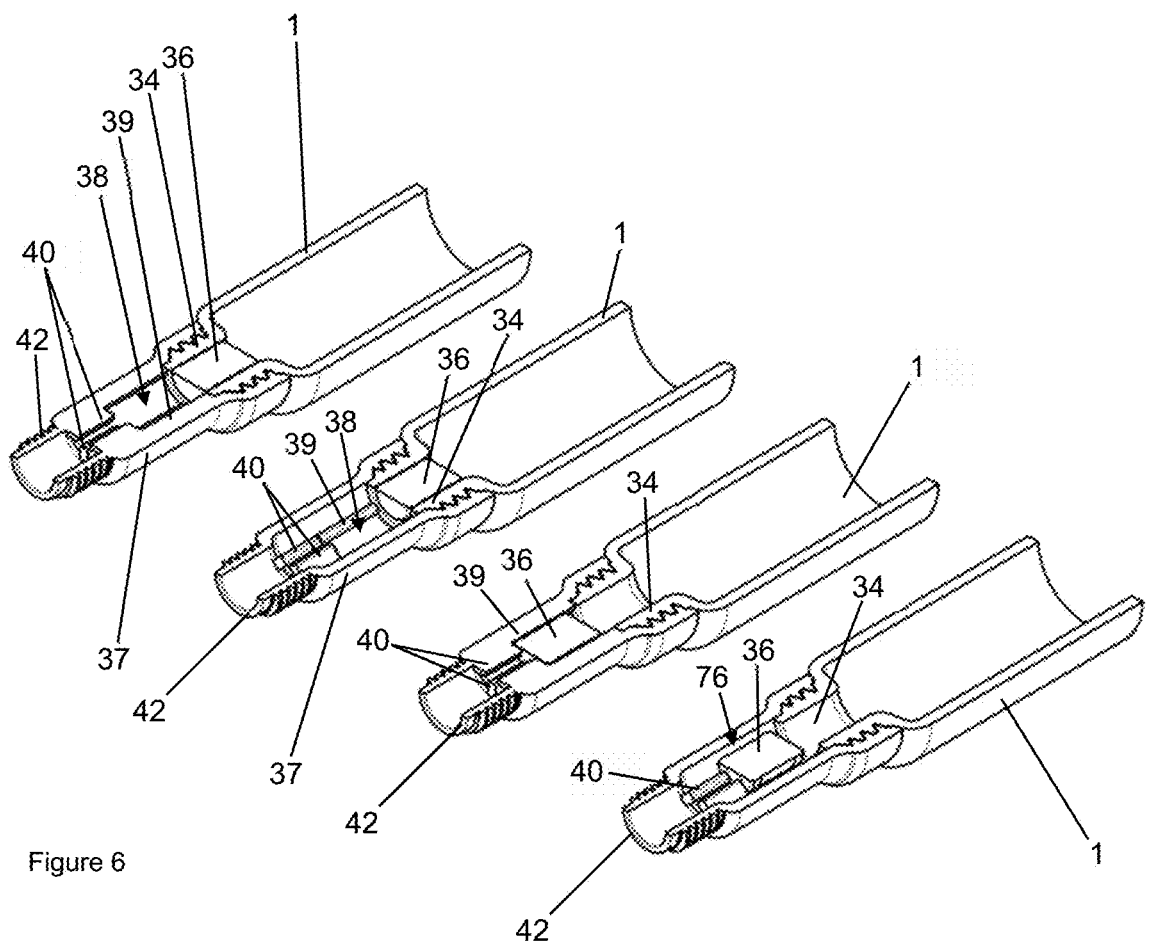
FIG. 6 illustrates four schematic perspective cross-sectional views of the front part of the device according to FIGS. 1 to 5 in the closed state and in the open state.
Figure 7:
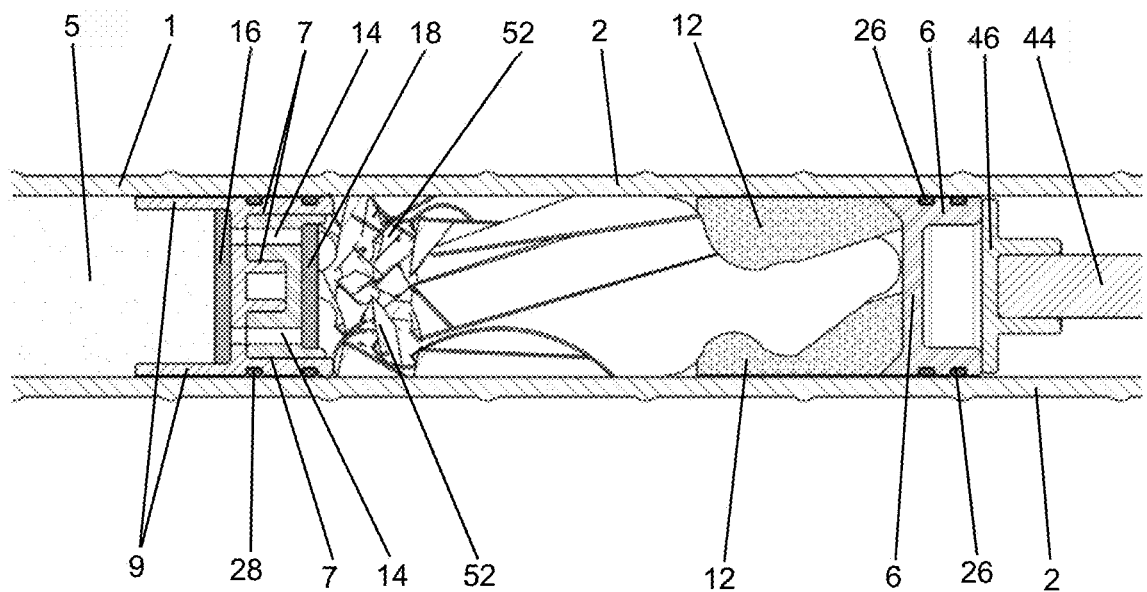
FIG. 7 illustrates a schematic cross-sectional view in the form of an enlarged detail of the device according to the second illustration from the top of FIG. 3 during pressing in of the monomer liquid.
Figure 8:
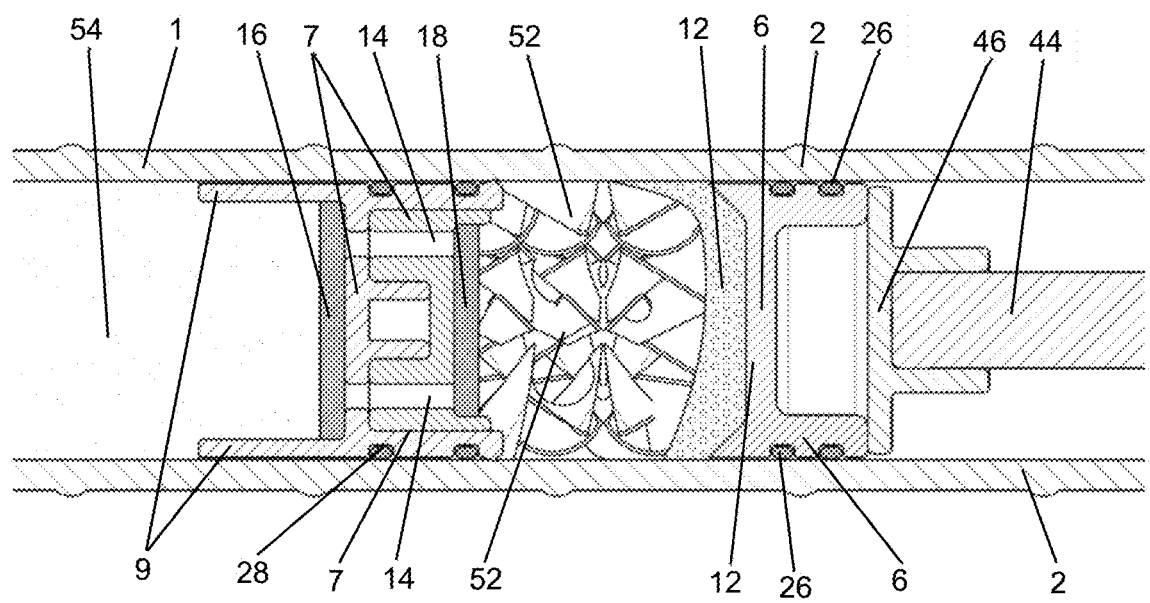
FIG. 8 illustrates a schematic cross-sectional view in the form of an enlarged detail of the device according to the third illustration from the top of FIG. 3 during pressing forward of the bone cement paste.

FIG. 6 illustrates four schematic perspective cross-sectional views of the front part of the device in the closed state (the two illustrations on the left-hand side) and in the open state (the two illustrations on the right-hand side). The cross-sectional planes here lie in the longitudinal axis of the device and are turned by 45° relative to one another, such that in the first illustration from top left and in the third illustration from top left the sections pass longitudinally through the bars 39, 40 and in the second illustration from top left and in the fourth illustration from top left the section passes between the bars 39, 40. As a result, in the cross-sectional view between the bars 39, 40 the free spaces and for example, the free line cross-section 76 remaining between the bars 39, the internal wall of the closure receptacle 38 and the circumferential surface of the closure 36 when the closure 36 is open (or when the closure 36 is sunk into the closure receptacle 38) are apparent. The bone cement paste may flow through the free line cross-section 76 and through the free spaces between the bars 40 when the closure 36 is open.

Figure 4:
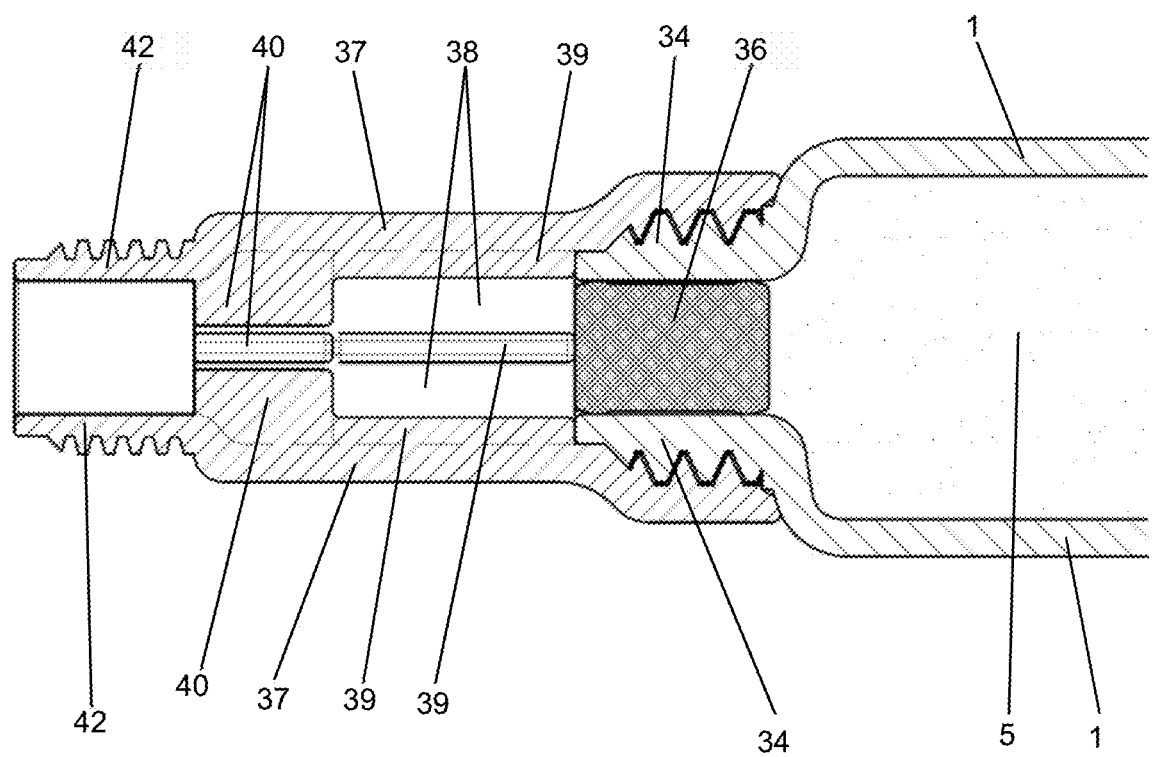
FIG. 4 illustrates a schematic cross-sectional view in the form of an enlarged detail through the front part of the device according to one embodiment according to FIGS. 1 to 3 in the closed state.
Figure 9:
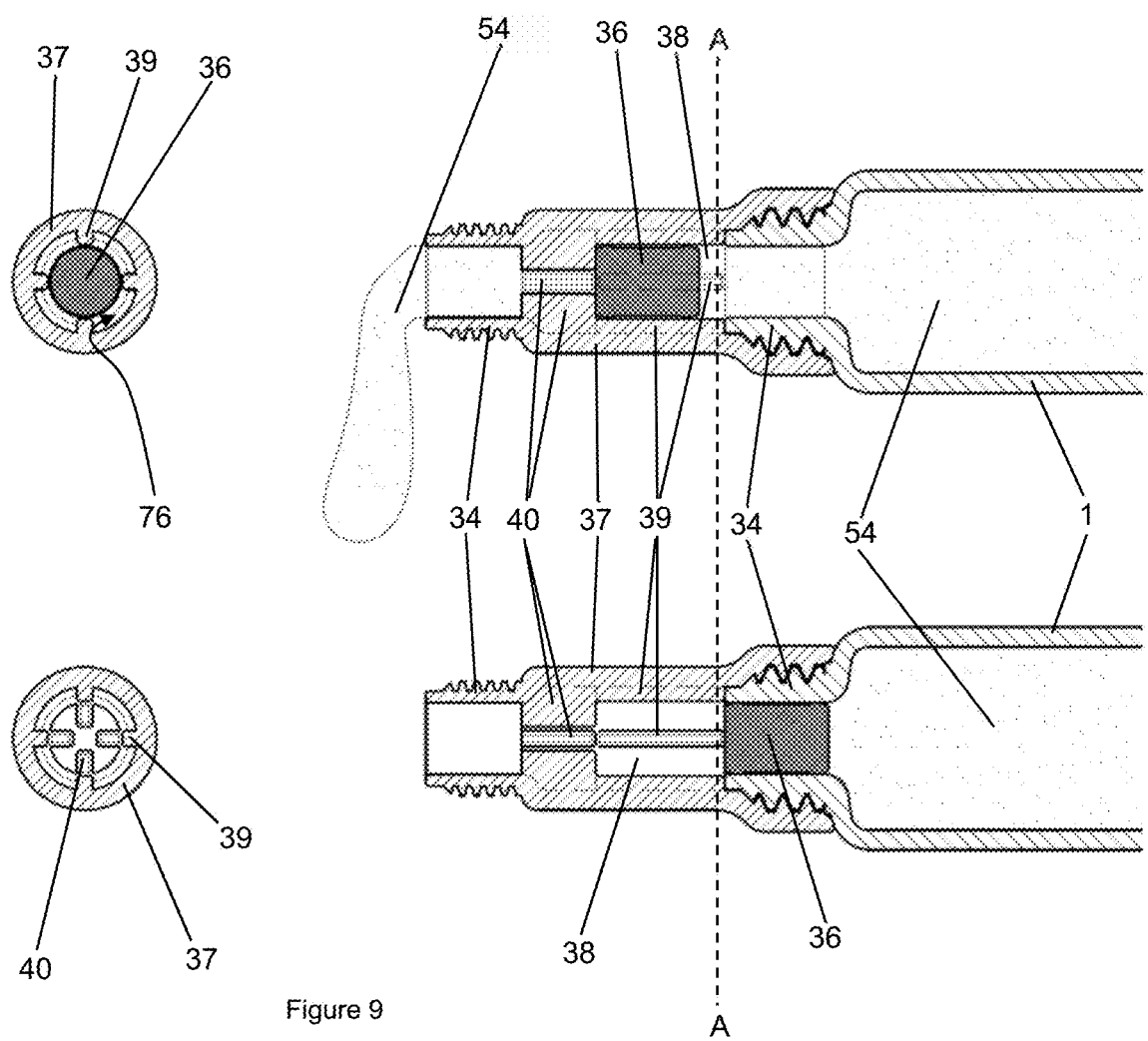
FIG. 9 illustrates four schematic cross-sectional views in the form of enlarged details of the front part of the device in the open and in the closed state.

FIG. 3 illustrates four schematic cross-sectional views one above the other of the device according to one embodiment to illustrate the sequence of a method according to one embodiment. In addition, FIG. 4 illustrates an enlarged detail of the first illustration from the top of FIG. 3, FIG. 7 an enlarged detail of the second illustration from the top of FIG. 3 and FIG. 8 an enlarged detail of the third illustration from the top of FIG. 3. The illustration top right in FIG. 9 illustrates an enlarged detail of the third illustration from the top of FIG. 3 and the illustration bottom right in FIG. 9 illustrates an enlarged detail of the second illustration from the top of FIG. 3. In addition, the illustration top left in FIG. 9 illustrates a perpendicular cross-sectional view along section plane A-A with a direction of view to the front (away from the cartridge 1) and the illustration bottom left in FIG. 9 illustrates a perpendicular cross-sectional view along section plane A-A with a direction of view to the front (away from the cartridge 1).

At the start of the method, the device is in the initial state, as illustrated also in FIG. 1. In this state, the device is inserted into an expulsion device 43, for example a conventional, manually hand-drivable cartridge gun. This situation is illustrated in the topmost illustration of FIG. 3. The expulsion device 43 includes a linearly advanceable rod 44. Only the front part of the expulsion device 43 is depicted. The expulsion device 43 also includes a handle and a trigger lever (not visible in the illustrations) for manually driving the rod 44 of the expulsion device 43, as is also the case with conventional manually driven expulsion devices. The device is fastened with the fastening means 8 to the expulsion device 43 (see topmost illustration in FIG. 3). A flat disc 46 is provided at the tip of the rod 44 to drive the conveying plunger 6. The rod 44 pushes on the conveying plunger 6 with the disc 46 when the rod 44 of the expulsion device 43 is pushed into the monomer receptacle 2. The expulsion device 43 is to this end connected via a mating fastening means 48 to the back side of the monomer receptacle 2, such that the disc 46 pushes on the conveying plunger 6 on advance of the rod 44 and advances it in the direction of the cartridge 1. To this end, the rod 44 is mounted so as to be linearly mobile relative to a bearing 50 and thereby relative to the mating fastening means 48 and thus relative to the monomer receptacle 2.

The expulsion device 43 is operated and in the process the rod 44 and, with the rod 44, the conveying plunger 6 are advanced in the direction of the cartridge 1. At the start of the movement of the conveying plunger 6, the latter closes the ventilation openings 20. The bearing 12 is compressed and the conveying plunger 6 meets the head of the glass ampoule 3. Since the glass ampoule 3 rests at the front side against the delivery plunger 7 and the interior of the monomer receptacle 2 becomes increasingly smaller, the glass ampoule 3 is broken. The monomer liquid 4 exits from the glass ampoule 3 into the interior of the monomer receptacle 2. The delivery plunger 7 cannot be pushed or cannot be pushed far by the glass ampoule 3 in the direction of the closure 36 when the cement powder 5 is dry, that is, has not been wetted by the monomer liquid 4, since the dry cement powder 5 is not flowable and blocks movement of the delivery plunger 7. This situation is illustrated in FIG. 3, second illustration from the top, and in the enlarged detail view in FIG. 7. Residual air from the monomer receptacle 2 is pushed out of the device through the filter 18, the connection 14, the porous filter 16, through the interspaces between the particles of the cement powder 5, through the closure 36 and out of the open line element 37 or out of an applicator tube 66 screwed onto the line element 37.

Ultimately, all that remains of the glass ampoule 3 is small splinters 52, which are retained by the filter 18 and remain in the tubular container. The monomer liquid 4 is pressed through the filter 18, the connection 14 and the porous filter 16 into the cement powder 5 and there begins to react with the cement powder 5, such that the bone cement paste 54 forms from the mixture 54. In this case, the monomer liquid 4 cannot flow directly out of the porous filter 16 to the internal wall of the cartridge 1, since this is completely or, in the case of a slotted hollow cylinder 9, largely concealed by the hollow cylinder 9. In this way, the monomer liquid 4 is forced to clear a path through the cement powder 5.

Monomer liquid bubbles or monomer liquid accumulations can be prevented in this way and a more homogeneous bone cement paste 54 is mixed than without use of the hollow cylinder 9.

The quantity of monomer liquid 4 is selected such that the cement powder 5 is wetted with the monomer liquid 4 as far as into the frontmost point of the cartridge 1, that is, as far as up to the closure 36. As soon as the mixture, that is, the bone cement paste 54, has arisen, the closure 36 is driven forwards by the pressure acting on the bone cement paste 54 due to the pressure on the delivery plunger 7 and pushed into the closure receptacle 38 until the closure 36 meets with the limit stop 40, at which point movement of the closure 36 terminates. This situation is illustrated in FIG. 3, third illustration from the top and in the detail views according to FIG. 8 and FIG. 9 top and in the two illustrations to the bottom right in FIG. 6. The bone cement paste 54 flows around the closure 36 by flowing through between the bars 39 and between the bars 40. Finally, the bone cement paste 54 exits at the front side of the device.

In this state (or alternatively right at the start) an applicator pipe 66 is screwed onto the outer thread of the fitting 42 as an extended delivery opening or in the form of a delivery pipe extension 70 (see also FIG. 5). By advancing the rod 44 further, the conveying plunger 6, the broken glass 52 and the delivery plunger 7 arranged in front thereof are driven. The bone cement paste 54 is then delivered from the cartridge 1 via the applicator tube 66. To this end, the delivery plunger 7 is advanced with the rod 44 in the direction of the line element 37 (see in this respect also the fourth illustration from the top in FIG. 3 and the detail view according to FIG. 8). The bone cement paste 54 is discharged from the interior of the cartridge 1 through the fitting 34, the line element 37 and the applicator tube 66 and may be applied there or theoretically used for further processing.

Finally, the hollow cylinder 9 meets with the cartridge head or the front side of the interior of the cartridge 1. Since the delivery plunger 7 is blocked at the end of the expulsion process, it may happen that the broken glass and splinters 52 from the glass ampoule 3 are compressed still further by the increasing pressure acting on the broken glass and splinters 52 and, in the process, yet further remnants of the monomer liquid 4 are pushed out of the interspace between the delivery plunger 7 and the conveying plunger 6 into the front part of the cartridge 1. This may result in a change in the composition of the bone cement paste 54, since the proportion of liquid monomer liquid 4 in the bone cement paste 54 is increased. When the bone cement paste 54 has already very largely reacted, it may also happen that the monomer liquid 4 forces its way past the bone cement paste 54. The hollow cylinder 9 has a height of 3 mm, in one embodiment of 5 mm or greater, such that it is ensured by the distance created thereby that the front side of the delivery plunger 7 is spaced from the front side of the interior of the cartridge 1 when the delivery plunger 7 has been pushed as far forwards as is possible with a manually driven expulsion device 43. This creates a dead volume in the interior of the cartridge 1, and specifically in the region delimited by the hollow cylinder 9, which cannot be discharged from the cartridge 1 through the delivery opening and the line element 37.

The part of the bone cement paste 54 which optionally contains too great a proportion of monomer liquid 4 is now located in this dead volume. Even if more pressure subsequently continues to be applied, no further bone cement paste 54 can be expelled out of the device from the dead volume. This structure ensures that no bone cement paste 54 of variable consistency due to a variable composition can be applied with the device.

Figure 10:
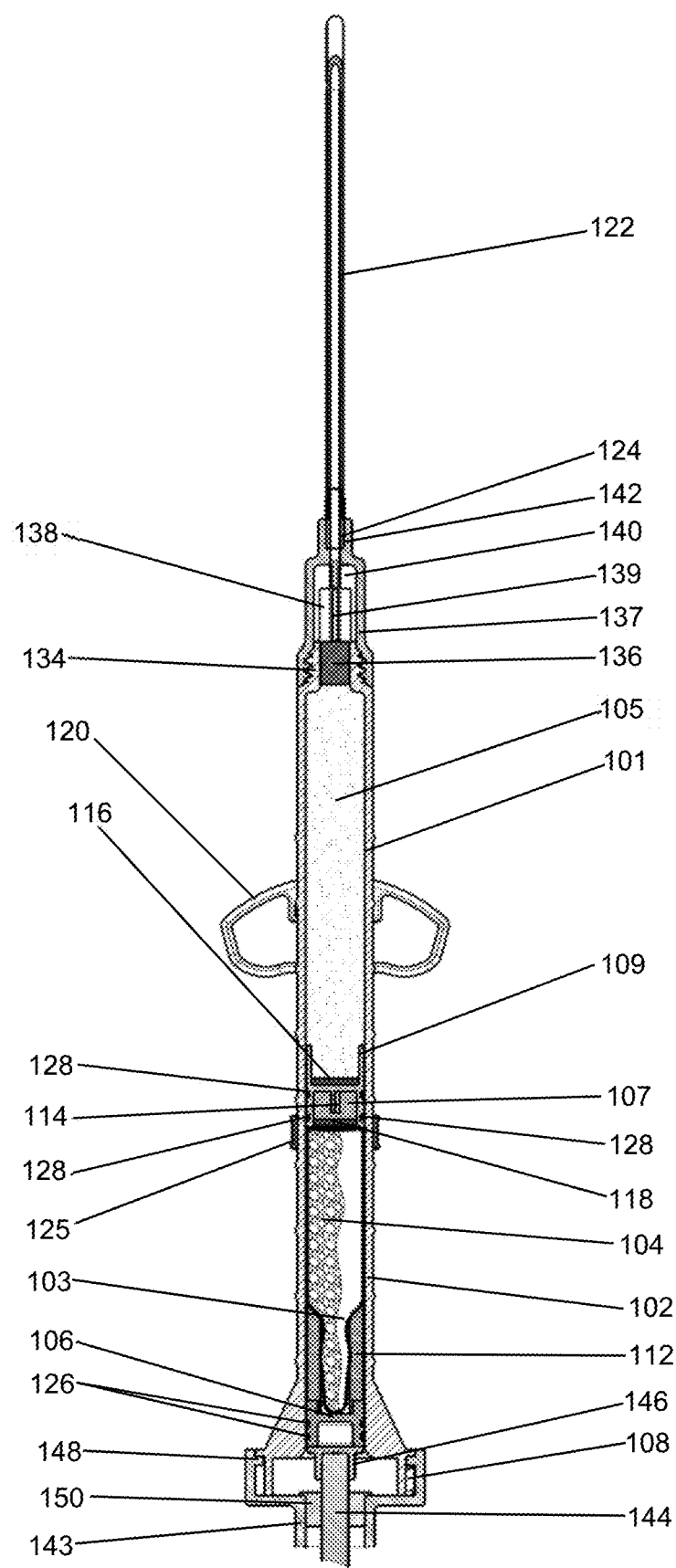
FIG. 10 illustrates a schematic cross-sectional view of a second exemplary device according to one embodiment for storing and mixing a monomer liquid and a cement powder, in the form of a spine applicator for spondylodesis with a connected expulsion device.
Figure 11:
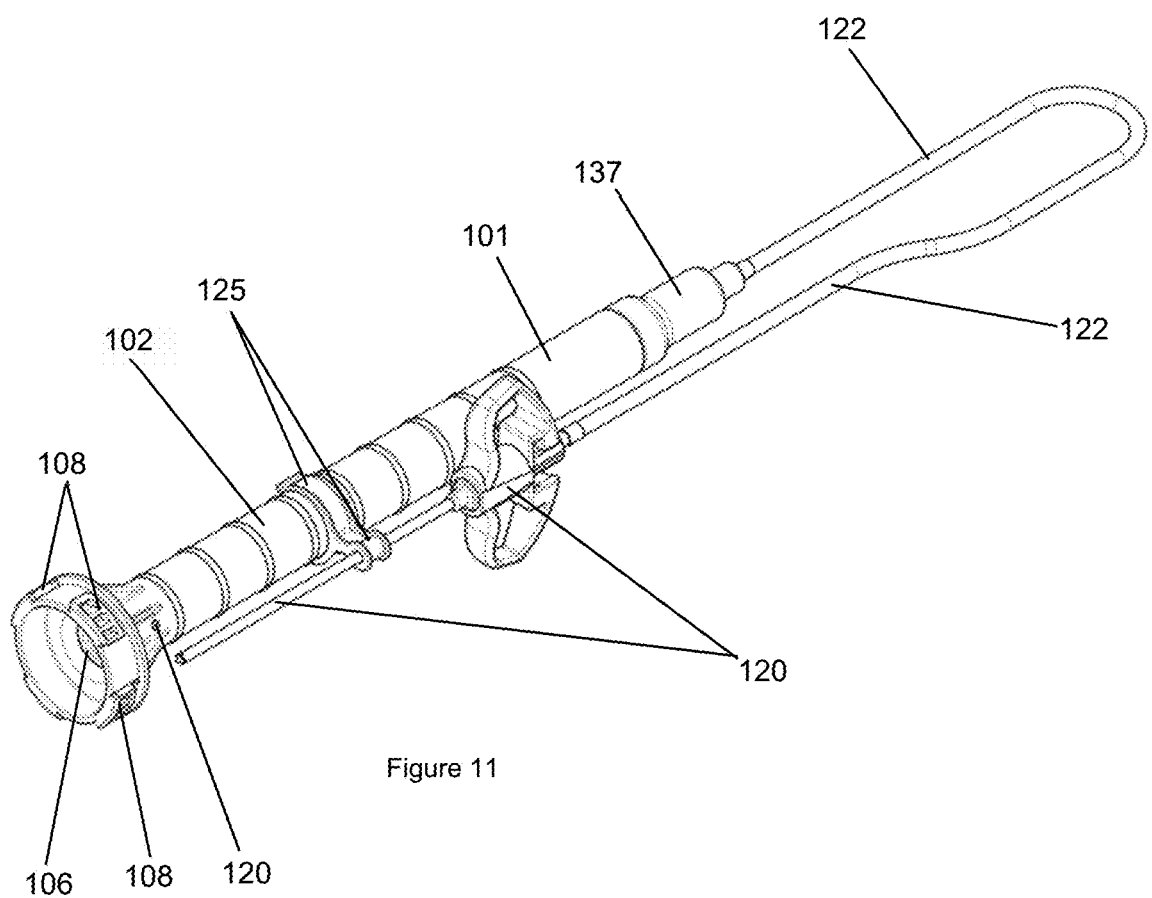
FIG. 11 illustrates a schematic perspective view of the spine applicator according to FIG. 10.
Figure 12:
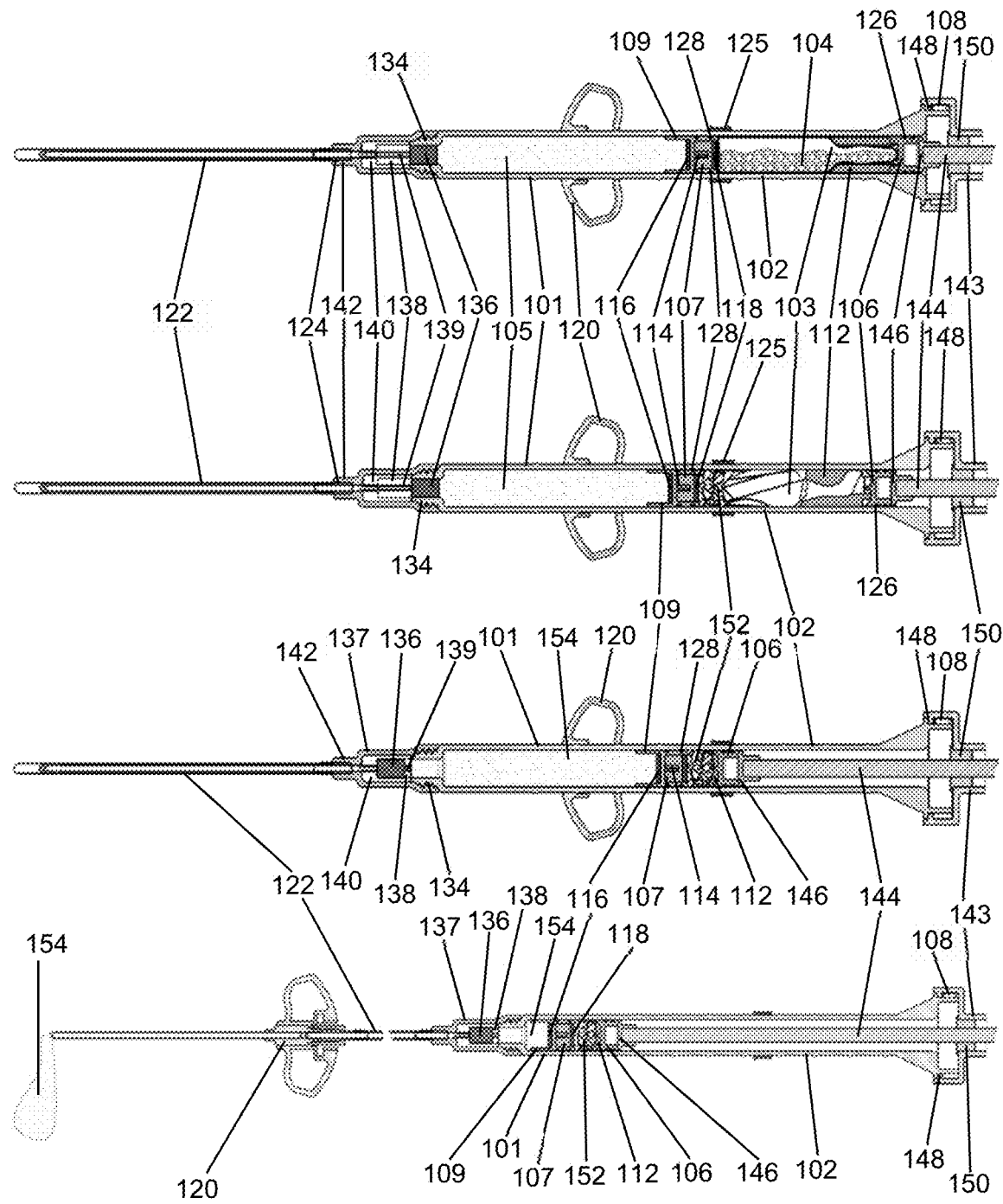
FIG. 12 illustrates four schematic cross-sectional views one above the other of the spine applicator according to FIGS. 10 and 11 with a connected expulsion device to illustrate the sequence of a method according to one embodiment.
Figure 13:
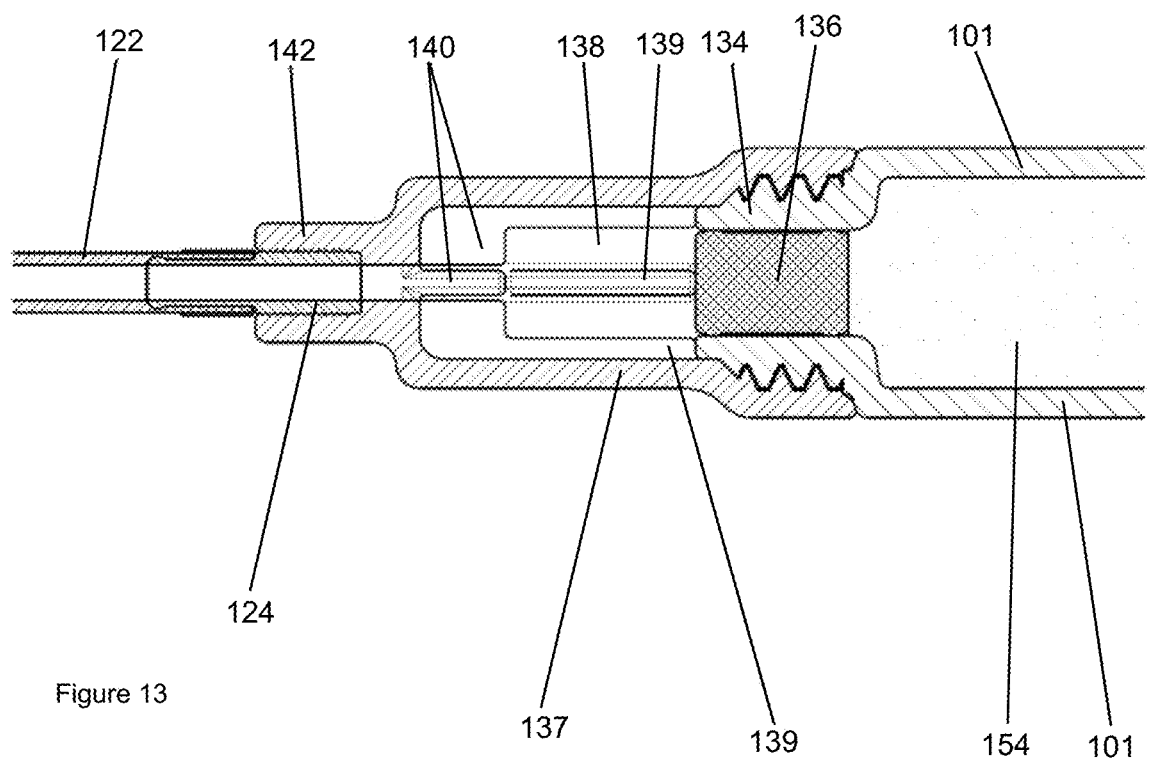
FIG. 13 illustrates a schematic cross-sectional view in the form of an enlarged detail through the front part of the spine applicator according to one embodiment according to FIGS. 10 to 12 in the closed state.
Figure 14:
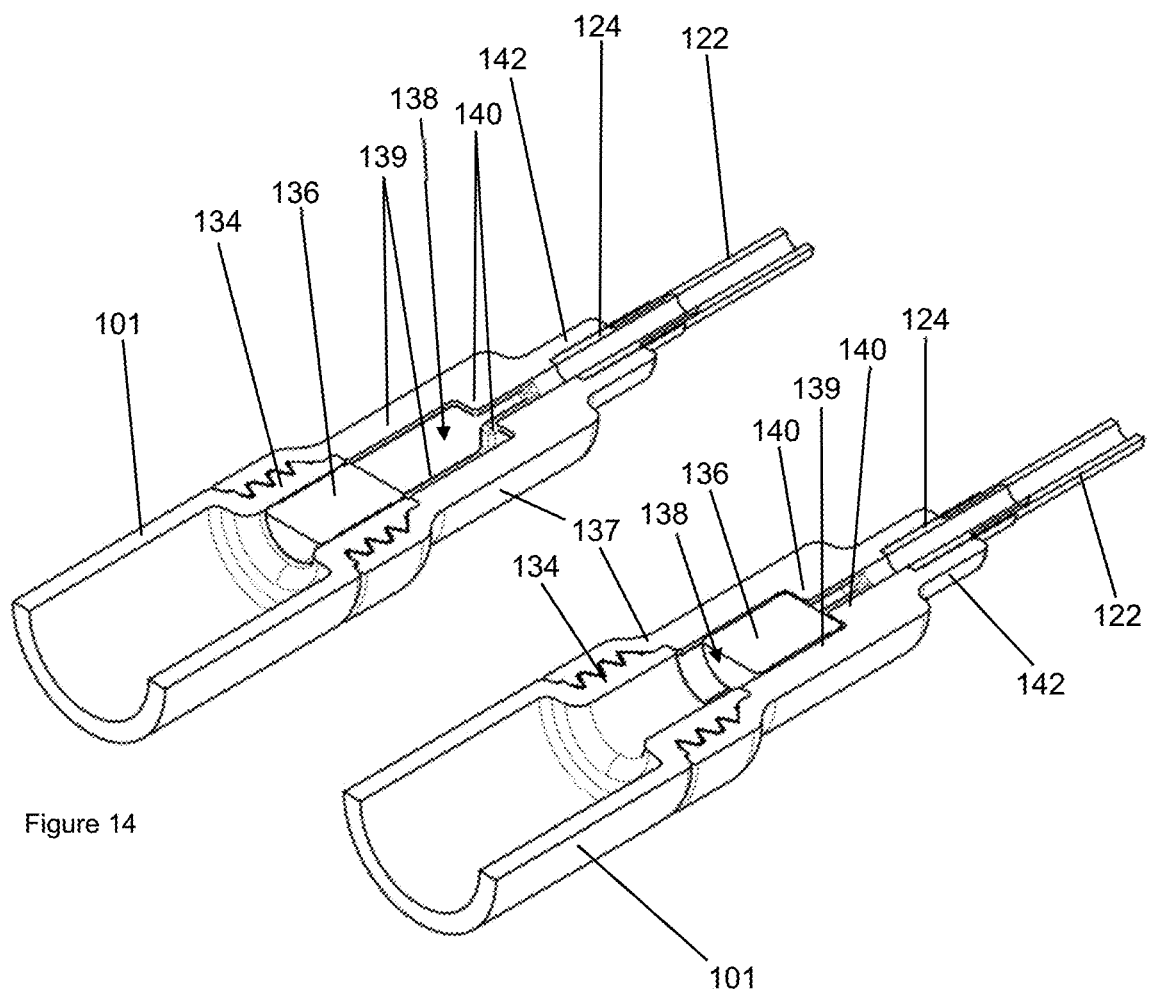
FIG. 14 illustrates two schematic perspective cross-sectional views of the front part of the spine applicator according to FIGS. 10 to 13 in the closed state and in the open state.
Figure 15:
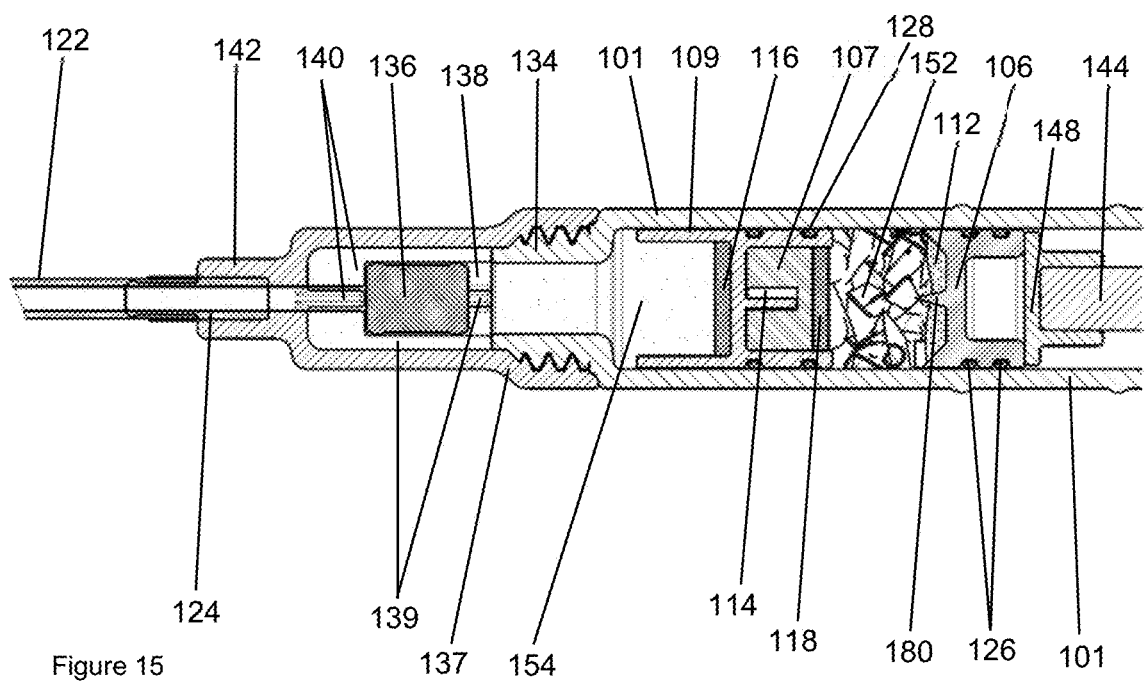
FIG. 15 illustrates a schematic cross-sectional view in the form of an enlarged detail of the spine applicator according to the last illustration from the top in FIG. 12.

FIGS. 10 to 15 illustrate illustrations of a second, alternative device according to one embodiment. FIGS. 10 to 12 illustrate various schematic overall views of the exemplary second device according to one embodiment. FIGS. 13 to 15 illustrate schematic cross-sectional views as detail views, in the form of enlarged details, through different regions of the second device according to one embodiment. The second device according to one embodiment is a "spine applicator" for spondylodesis. It is used for spinal fusion or spinal stabilization of two vertebrae, bone cement paste 154 being applied in the vertebral region under X-ray monitoring with the assistance of a trocar 120. As a result of the trocar 120, the surgeon does not have to operate in the path of the X-radiation.

The second device according to one embodiment is largely identical in structure to the first device according to one embodiment according to FIGS. 1 to 9 and consists substantially of a tubular container of plastic, which forms a cartridge 101 with cylindrical interior as the front part (top in FIG. 10, top right in FIGS. 11 and 14, to the left in FIGS. 12, 13 and 15) and which forms a monomer receptacle 102 for a glass ampoule 103 as monomer liquid container as the rear part. Instead of the glass ampoule 103, a break-openable plastic ampoule may also straightforwardly be used or, with minor alterations, a tear-openable film pouch consisting of a metal-coated plastic may also be used instead of the glass ampoule 103.

The back side of the device is illustrated at the bottom in FIG. 10, to the right in the illustrations of FIG. 12 and bottom left in FIG. 11. The tubular shape of the container is particularly apparent in the cross-sectional views of FIGS. 10 and 12 and the perspective view according to FIG. 11. Both the interior of the cartridge 101 and the interior of the monomer receptacle 102 are cylindrical with a circular base area. In this respect, the diameter of the interior of the cartridge 101 and the diameter of the interior of the monomer receptacle 102 are identical in size and aligned. The container with the monomer receptacle 102 and the cartridge 101 is in one embodiment produced from plastic using injection molding technology. The monomer receptacle 102 thus has a cylindrical interior, into which the glass ampoule 103 has been placed. The glass ampoule 103 contains the monomer liquid 104. In FIG. 10 the device is illustrated turned on its side, such that gravity works sideways and the monomer liquid 104 collects on one side of the glass ampoule 103. A cement powder 105 has been poured or in one embodiment pressed into the interior of the cartridge 101. The monomer liquid 104 and the cement powder 105 form the parent components for a PMMA bone cement, which is producible using the device. Owing to the glass ampoule 103, the monomer liquid 104 can be stored for a very long time in the monomer receptacle 102 and thereby in the device. The cement powder 105 can likewise be stored for extended periods in the device. The device is thus suitable for storing the monomer liquid 104 and the cement powder 105 as parent components of a bone cement paste 154 of the PMMA bone cement. The device is, however, also suitable and provided for mixing the bone cement paste 154 from the parent components 104, 105 and for delivering the mixed bone cement paste 154.

Arranged in the monomer receptacle 102 is a conveying plunger 106 of plastic movable in the longitudinal direction in the cylindrical interior of the monomer receptacle 102. The conveying plunger 106 is arranged in the region of the back side of the monomer receptacle 102. The glass ampoule 103 may be compressed, and shattered in the process, in the monomer receptacle 102 using the conveying plunger 106, in that the conveying plunger 106 is pushed in the direction of the front side, that is, in the direction of the cartridge 101. The conveying plunger 106 has wipers at the front side with which splinters of the glass ampoule 103 are wiped off the internal wall of the monomer receptacle 102. To this end, the wipers rest laterally against the internal wall of the interior of the monomer receptacle 102. Furthermore, an edge 180 is arranged at the front side of the conveying plunger 106, which simplifies breaking open of the glass ampoule 103 on advance of the conveying plunger 106 in the monomer receptacle 102.

A delivery plunger 107 of plastic is arranged in the interior of the cartridge 101, in the back side thereof (towards the bottom in FIG. 10, towards the right in FIGS. 12 and 15). At the back side of the monomer receptacle 102 a fastening means 108 is provided, with which the monomer receptacle 102 and/or the container may be connected to an expulsion device 143 (not visible in FIG. 11 but see FIGS. 10 and 12). The fastening means 108 is in one embodiment suitable and provided for forming a bayonet closure 108. The conveying plunger 106, which is freely accessible from the back side of the monomer receptacle 102, can thereby be advanced with the expulsion device 143 in the direction of the front side of the cartridge 101.

At its front side, the delivery plunger 107 has a hollow cylinder 109 for extending the distance over which the monomer liquid 104 must flow through the cement powder 105 until it reaches the internal wall of the cartridge 101. In addition, the hollow cylinder 109 serves to space the delivery plunger 107 from a delivery opening at the front side of the interior of the cartridge 101 and to create a dead volume between the delivery plunger 107 and the front side of the interior of the cartridge 101 when the delivery plunger 107 or the hollow cylinder 109 is pushed to the greatest possible extent against the front side of the interior of the cartridge 101. In the present case, the hollow cylinder 109 is rotationally symmetrical and is shaped in the manner of a tube section. The hollow cylinder 109 may, however, also have longitudinal cuts extending parallel to the cylinder axis of the hollow cylinder 109. At the front side the hollow cylinder 109 is planar.

In the interior of the monomer receptacle 102 a bearing 112 of foam is provided which serves as a transport safeguard and as an impact safeguard for the glass ampoule 103. In this way it is intended to prevent the glass ampoule 103 from breaking open unintentionally in the event of vibrations or impacts. The foam and thus the bearing 112 are gas-permeable.

The cartridge 101 and the monomer receptacle 102 are embodied in one piece as a joint plastics part. The monomer receptacle 102 and the cartridge 101 are connected together via a connection 114 in the delivery plunger 107 in a liquid-permeable manner for the monomer liquid 104. The connection 114 through the delivery plunger 107 leads through a porous filter 116 impermeable to the cement powder 105 but permeable to the monomer liquid 104 into the interior of the cartridge 101.

At the mouth leading to the connection 114 a filter 118 is arranged in the delivery plunger 107, with which filter the splinters 152 of the glass ampoule 103 can be held back. A screen may also be provided instead of the filter 118 or in addition to the filter 118.

A plurality of ventilation openings 120 are provided in the wall of the monomer receptacle 102, through which the interior of the monomer receptacle 102 may be sterilized by means of a sterilizing gas such as ethylene oxide. The bearing 112 is likewise gas-permeable and therefore does not close the ventilation openings 120. The ventilation openings 120 are arranged directly adjacent the conveying plunger 106, such that the conveying plunger 106 is pushed directly in front of the ventilation openings 120 and thus directly closes the ventilation openings 120 when the conveying plunger 106 is advanced in the direction of the cartridge 101. This prevents monomer liquid 104 from being able to escape through the ventilation openings 120 when the glass ampoule 103 in the monomer receptacle 102 has been opened.

The cylindrical conveying plunger 106 has an outer circumference which matches the cylindrical geometry of the interior of the monomer receptacle 102 and is sealed in liquid-tight manner relative to the internal wall of the monomer receptacle 102 via two circumferential seals 126. The delivery plunger 107 is likewise sealed in liquid-tight manner relative to the internal wall of the cartridge 101 via two circumferential seals 128. These seals 126, 128 serve to prevent monomer liquid 104 or bone cement from escaping, so as to prevent contamination of the surrounding environment (the operating room and the user). To this end, the seals 126, 128 may consist of rubber.

The interior of the cartridge 101 leads at the front side into a fitting 134, which defines the delivery opening of the cartridge 101. The fitting 134 has an outer thread. Inside the fitting 134 a closure 136 for the cartridge 101 is arranged, which is lodged in the delivery opening and closes it. The closure 136 is a porous filter impermeable to the cement powder 105 but permeable to gases and has a cylindrical shape.

A line element 137 with a closure receptacle 138 for receiving the closure 136 is fastened to the outer thread of the fitting 134. The closure receptacle 138 is shaped in the manner of a sleeve and has four longitudinally oriented bars 139 extending into the closure receptacle 138. The bars 139 space the closure 136 from the internal wall of the closure receptacle 138 when the closure 136 has been pushed into the closure receptacle 138. The line element 137 narrows in front of the closure receptacle 138. In this region four further bars 140 are arranged, which form a limit stop 140 for movement of the closure 136 and thus limit movement of the closure 136 into the closure receptacle 138. A sufficiently large free line cross-section is provided between the bars 139, 140, such that the bone cement paste 154 may flow through between the bars 139, the wall of the closure receptacle 138 and the pushed-in closure 136 and between the bars 140 in the front part of the line element 137. At the front side thereof, the line element 137 terminates in a fitting 142 with an inner thread.

A trocar 120 and a hose 122 for connecting the trocar 120 are connected to the line element 137. To this end, insert 124 with a matching outer thread is screwed into the inner thread of the fitting 142, wherein the insert is connected with the hose 122 via a crimped connection. The trocar 120 is also connected with the hose 122 via a crimped connection. A holder 125 is fastened to the outside of the container 101, 102, onto which holder an application tip of the trocar 120 may be clipped so that the trocar 120 does not dangle loose from the device.

Through the closure 136 embodied as a porous filter, the inside of the cartridge 101 and the cement powder 105 may be sterilized using ethylene oxide, since the line element 137 is open, the trocar 120 has not yet been connected to the hose 122 at the time of sterilization and the closure 136 and the interspaces between the powder particles of the cement powder 105 are air-permeable At the same time, air may be expelled from the monomer receptacle 102 through the cement powder 105, the closure 136, the line element 137, the hose 122 and the trocar 120 when the conveying plunger 106 is pressed in the direction of the delivery plunger 107.

The cement powder 105 is enclosed in the cartridge 101, since all the openings and connections 114 are closed in a manner impermeable to the cement powder 105 by means of the porous filters 116, 136. The contents of the cartridge 101 may in this respect be sterilized by evacuation and flushing with ethylene oxide. This renders the device also suitable for long-term storage of the cement powder 105.

FIG. 14 illustrates two schematic perspective cross-sectional views of the front part of the device in the closed state (illustration on the left-hand side) and in the open state (illustration on the right-hand side). As in the first exemplary embodiment, in the open state the closure 136 is spaced from the internal wall of the closure receptacle 138 by the bars 139. This results in the formation therebetween of a free line cross-section through which the bone cement paste 154 may be expelled from the device through the line element 137, through the hose 122 and through the trocar 120.

FIG. 12 illustrates four schematic cross-sectional views one above the other of the second device according to one embodiment to illustrate the sequence of a method according to one embodiment. In addition, FIG. 13 illustrates an enlarged detail of the first illustration from the top of FIG. 12 and FIG. 15 illustrate an enlarged detail of the fourth illustration from the top of FIG. 12. The illustration to the right in FIG. 14 illustrates an enlarged detail of the third illustration from the top of FIG. 12 and the illustration to the left in FIG. 14 illustrates an enlarged detail of the second illustration from the top of FIG. 12.

At the start of the method, the device is in the initial state, as illustrated also in FIG. 10. In this state, the device is inserted into the expulsion device 143, for example a conventional, manually hand-drivable cartridge gun. This situation is illustrated in the topmost illustration of FIG. 12. The expulsion device 143 includes a linearly advanceable rod 144. Only the front part of the expulsion device 143 is depicted. The expulsion device 143 also includes a handle and a trigger lever (not visible in the illustrations) for manually driving the rod 144 of the expulsion device 143, as is also the case with conventional manually driven expulsion devices. The device is fastened with the fastening means 108 to the expulsion device 143 (see topmost illustration in FIG. 12). A flat disc 146 is provided at the tip of the rod 144 to drive the conveying plunger 106. The rod 144 pushes on the conveying plunger 106 with the disc 146 when the rod 144 of the expulsion device 143 is pushed into the monomer receptacle 102. The expulsion device 143 is to this end connected via a mating fastening means 148 to the back side of the monomer receptacle 102, such that the disc 146 pushes on the conveying plunger 106 on advance of the rod 144 and advances it in the direction of the cartridge 101. To this end, the rod 144 is mounted so as to be linearly mobile relative to a bearing 150 and thereby relative to the mating fastening means 148 and thus relative to the monomer receptacle 102.

The expulsion device 143 is operated and in the process the rod 144 and, with the rod 144, the conveying plunger 106 are advanced in the direction of the cartridge 101. At the start of the movement of the conveying plunger 106, the latter closes the ventilation openings 120. The bearing 112 is compressed and the conveying plunger 106 meets the head of the glass ampoule 103. Since the glass ampoule 103 rests at the front side against the delivery plunger 107 and the interior of the monomer receptacle 102 becomes increasingly smaller, the glass ampoule 103 is broken. The monomer liquid 104 exits from the glass ampoule 103 into the interior of the monomer receptacle 102. The delivery plunger 107 cannot be pushed or cannot be pushed far by the glass ampoule 103 in the direction of the closure 136 when the cement powder 105 is dry, that is, has not been wetted by the monomer liquid 104, since the dry cement powder 105 is not flowable and blocks movement of the delivery plunger 107. This situation is illustrated in FIG. 12, second illustration from the top, and in the enlarged detail view in FIG. 13. Residual air from the monomer receptacle 102 is pushed out of the device through the filter 118, the connection 114, the porous filter 116, through the interspaces between the particles of the cement powder 105, through the closure 136, through the line element 137, and through the hose 122 and the trocar 120.

Ultimately, all that remains of the glass ampoule 103 is small splinters 152, which are retained by the filter 118 and remain in the tubular container. The monomer liquid 104 is pressed through the filter 118, the connection 114 and the porous filter 116 into the cement powder 105 and there begins to react with the cement powder 105, such that the bone cement paste 154 forms from the mixture. In this case, the monomer liquid 104 cannot flow directly out of the porous filter 116 to the internal wall of the cartridge 101, since this is completely or, in the case of a slotted hollow cylinder 109, largely concealed by the hollow cylinder 109. In this way, the monomer liquid 104 is forced to clear a path through the cement powder 105. Monomer liquid bubbles or monomer liquid accumulations can be prevented in this way and a more homogeneous bone cement paste 154 is mixed than without use of the hollow cylinder 109.

The quantity of monomer liquid 104 is selected such that the cement powder 105 is wetted with the monomer liquid 104 as far as into the frontmost point of the cartridge 101, that is, as far as up to the closure 136. As soon as the mixture, that is, the bone cement paste 154, has arisen, the closure 136 is driven forwards by the pressure acting on the bone cement paste 154 due to the pressure on the delivery plunger 107 and pushed into the closure receptacle 138 until the closure 136 meets with the limit stop 140, at which point movement of the closure 136 terminates. This situation is illustrated in FIG. 12, third illustration from the top and in the detail view according to FIG. 14. The bone cement paste 154 flows around the closure 136, by flowing through between the bars 139 and between the bars 140. Then the bone cement paste 154 is pressed through the hose 122 and into the trocar 120. The bone cement paste 154 may flow out of the trocar 120 at the front side of the device.

By advancing the rod 144 further, the conveying plunger 106, the broken glass 152 and the delivery plunger 107 arranged in front thereof are driven. The bone cement paste 154 is then delivered out of the cartridge 101 via the hose 122 and the trocar 120. To this end, the delivery plunger 107 is advanced with the rod 144 in the direction of the line element 137 (see in this respect also the fourth illustration from the top in FIG. 12 and the detail view according to FIG. 15).

Finally, the hollow cylinder 109 meets with the cartridge head or the front side of the interior of the cartridge 101. Since the delivery plunger 107 is blocked at the end of the expulsion process, it may happen that the broken glass and splinters 152 from the glass ampoule 103 are compressed still further by the increasing pressure acting on the broken glass and splinters 152 and, in the process, yet further remnants of the monomer liquid 104 are pushed out of the interspace between the delivery plunger 107 and the conveying plunger 106 into the front part of the cartridge 101. This may result in a change in the composition of the bone cement paste 154, since the proportion of liquid monomer liquid 104 in the bone cement paste 154 is increased. When the bone cement paste 154 has already very largely reacted, it may also happen that the monomer liquid 104 forces its way past the bone cement paste 154. The hollow cylinder 109 has a height of 3 mm, in one embodiment of 5 mm or greater, such that it is ensured by the distance created thereby that the front side of the delivery plunger 107 is spaced from the front side of the interior of the cartridge 1 when the delivery plunger 107 has been pushed as far forwards as is possible with a manually driven expulsion device 143. This creates a dead volume in the interior of the cartridge 101, and specifically in the region delimited by the hollow cylinder 109, which cannot be discharged from the cartridge 101 through the delivery opening, the hose 122 and the trocar 120.

The part of the bone cement paste 154 which optionally contains too great a proportion of monomer liquid 104 is now located in this dead volume. Even if more pressure subsequently continues to be applied, no further bone cement paste 154 can be expelled out of the device from the dead volume. This structure ensures that no bone cement paste 154 of variable consistency due to a variable composition can be applied with the device.

The features disclosed in the above description, as well as in the claims, figures and exemplary embodiments, may be important both individually and in any desired combination to realization of the various embodiments.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A device for producing a bone cement paste from a monomer liquid and a cement powder as parent components of the bone cement paste and for delivering the bone cement paste, the device comprsing:
    a cartridge with a cylindrical interior, in which the parent components are mixable, the interior of the cartridge being closed at a front side apart from a delivery opening for discharging the bone cement paste from the interior;
    a delivery plunger arranged in the interior of the cartridge and mounted so as to be pushable in a direction of the delivery opening;
    wherein the interior of the cartridge between the delivery opening and the delivery plunger contains the cement powder;
    a closure that closes the delivery opening and that is mounted so as to be movable relative to the delivery opening; and
    a pipe line element arranged at a front side of the delivery opening, wherein the pipe line element comprises a closure receptacle for receiving at least a part of the closure;
    wherein the closure is pushable into the closure receptacle by pressure on the bone cement paste, in such a way that the delivery opening is opened; and
    wherein, when the closure has been pushed into the closure receptacle, the pipe line element provides a free line cross-section through which the bone cement paste is pushable out through the delivery opening and out of the device.

2. The device according to claim 1, wherein the bone cement paste flows around the closure in the closure receptacle when the bone cement paste flows through the pipe line element, and the bone cement paste flows along at least one side face or circumferential surface of the closure past the closure.

3. The device according to any claim 1, wherein the free line cross-section is delimited on one side at least in areas by the closure by a side face or a circumferential surface of the closure.

4. The device according to claim 1, wherein the closure becomes firmly lodged in the closure receptacle when it has been pushed out of the delivery opening into the closure receptacle.

5. The device according to claim 1, wherein the closure is cylindrical at least in parts, and the closure receptacle forms a hollow-cylindrical sleeve, wherein at least one channel is provided in a circumferential surface of the hollow-cylindrical sleeve, and wherein the at least one channel provides the free line cross-section.

6. The device according to claim 5, wherein an internal diameter of the hollow-cylindrical sleeve is greater than an external diameter of the closure, and is between 1 mm and 10 mm greater than the external diameter of the closure.

7. The device according to claim 5, wherein an axial length of the interior of the hollow-cylindrical sleeve is greater than an axial length of the closure, and is between 1 mm and 20 mm greater than the axial length of the closure.

8. The device according to claim 1, wherein spacers are provided in the closure receptacle for spacing the closure from the internal wall of the closure receptacle, wherein the spacers are bars that are oriented in a direction of movement of the closure and/or are oriented in a direction of flow of the bone cement paste.

9. The device according to claim 1, wherein the free line cross-section is at least half as large as a cross-section of the delivery opening.

10. The device according to claim 1, wherein the length of the closure is greater in its direction of movement than a width in directions perpendicular thereto.

11. The device according to claim 1, wherein a limit stop for limiting movement of the closure is arranged in the closure receptacle at a front end wall of the closure receptacle which is remote from the delivery opening, and wherein the limit stop spaces the closure, when fully pushed in, from the front end wall at the front side of the closure receptacle, such that the free line cross-section remains between the front side of the closure and the front end wall.

12. The device according to claim 1, the device having a monomer receptacle in which the monomer liquid is contained, wherein a back side of the cartridge is connected with a front side of the monomer receptacle, and connected in such a way that the interior of the cartridge is aligned with an interior of the monomer receptacle.

13. The device according to claim 12, wherein the interior of the monomer receptacle and the interior of the cartridge are connected together via a connection which is permeable to the monomer liquid and to monomer gases but impermeable to the cement powder.

14. The device according to claim 12, wherein the interior of the monomer receptacle is cylindrical and in which a monomer liquid container containing the monomer liquid, is arranged.

15. The device according to claim 12, wherein a conveying plunger movable in a longitudinal direction of the receptacle is arranged in the monomer receptacle, which conveying plunger is advanceable from a back side of the monomer receptacle in a direction of the front side, wherein a monomer liquid container containing the monomer liquid, is arranged between the conveying plunger and the delivery plunger.

16. The device according to claim 12, wherein at least one ventilation opening, which connects the interior of the monomer receptacle with the surrounding environment, is arranged in the wall of the monomer receptacle.

17. The device according to claim 1, wherein a fastening means is arranged on a back side of the device for fastening an expulsion device with which the delivery plunger is pushable in the direction of the delivery opening.

18. The device according to claim 1, wherein a hollow cylinder is arranged at a front side of the delivery plunger facing the delivery opening, wherein the hollow cylinder is open at its front side facing the delivery opening and extends from the front side of the delivery plunger at least 3 mm into the interior of the cartridge.

19. The device according to claim 18, wherein the hollow cylinder blocks further movement of the delivery plunger in the direction of the front side of the cartridge when the front side of the hollow cylinder rests against the front side of the interior of the cartridge, such that the delivery plunger is spaced from the front side of the interior of the cartridge and a dead volume remains in the interior of the cartridge.

20. The device according to claim 1, wherein, in the delivery plunger, at least one connection is provided from the back side of the delivery plunger to the front side of the delivery plunger for introducing the monomer liquid into the interior of the cartridge, wherein the at least one connection is permeable to the monomer liquid and to monomer gases and impermeable to the cement powder and wherein the at least one connection leads from the delivery plunger inside the hollow cylinder or through lines in the hollow cylinder at the front side of the hollow cylinder into the interior of the cartridge.

21. The device according to claim 1, wherein the closure has an indentation at the back side facing the interior of the cartridge, in which indentation a frontmost part of the cement powder is contained.

22. The device according to claim 1, wherein the volume of the closure receptacle is sufficient to accommodate the closure completely.

23. A method for producing a polymethyl methacrylate bone cement paste, wherein the bone cement paste is produced from a cement powder and a monomer liquid using a device according to claim 1, the method comprising:
  a) pushing the monomer liquid into the interior of the cartridge, such that the monomer liquid mixes with the cement powder and there forms the bone cement paste;
  b) pushing the bone cement paste with the delivery plunger in a direction of a front side of the cartridge;
  c) pushing the closure into the closure receptacle by the pressure of the bone cement paste acting on the closure and the delivery opening is opened in the process;
  d) wherin the bone cement paste flows through the pipe line element through a free line cross-section and is delivered from the device.

24. The method according to claim 23, wherein the device is inserted into an expulsion device prior to step a), the expulsion device having an axially advanceable rod, wherein the delivery plunger is advanced with the rod in a direction of the delivery opening of the cartridge.

25. The method according to claim 24, wherein, after insertion of the device into the expulsion device, a conveying plunger, which is mounted movably inside a monomer receptacle arranged on the back side of the cartridge at a back side of the monomer receptacle, is advanced with the rod in a direction of the cartridge, wherein through movement of the conveying plunger a monomer liquid container, in which the monomer liquid is contained, is opened and the monomer liquid is pressed out of the monomer receptacle into the cartridge, wherein the cement powder mixes with the monomer liquid in the interior of the cartridge to yield the bone cement paste.

26. The method according to claim 23, wherein a hollow cylinder is arranged at a front side of the delivery plunger facing the delivery opening, wherein the monomer liquid flows around the hollow cylinder before arriving at the internal wall of the cartridge and/or the delivery plunger meets with a front side of the cartridge, wherein further movement of the delivery plunger in the direction of the delivery opening is blocked with the hollow cylinder and a residual quantity of the bone cement paste remains in the part of the interior of the cartridge delimited by the hollow cylinder.

27. The method according to claim 23, wherein, in step a), the monomer liquid is pressed through at least one connection in the delivery plunger impermeable to the cement powder but permeable to gases and the monomer liquid into the cartridge, and is pressed into the cartridge by movement of a conveying plunger which is driven with the rod of the expulsion device.

* * * * *